(12) United States Patent
Ho et al.

(10) Patent No.: US 9,063,351 B1
(45) Date of Patent: Jun. 23, 2015

(54) INPUT DETECTION SYSTEM

(71) Applicant: Google Inc., Mountain View, CA (US)

(72) Inventors: Harvey Ho, Mountain View, CA (US); Nathan Pletcher, Mountain View, CA (US); Olivia Hatalsky, Berkeley, CA (US)

(73) Assignee: Google Inc., Mountain View, CA (US)

( * ) Notice: Subject to any disclaimer, the term of this patent is extended or adjusted under 35 U.S.C. 154(b) by 280 days.

(21) Appl. No.: 13/630,864

(22) Filed: Sep. 28, 2012

(51) Int. Cl.
    *G02C 7/00*     (2006.01)
    *A61B 3/00*     (2006.01)
    *G02C 7/04*     (2006.01)

(52) U.S. Cl.
    CPC .......................................... *G02C 7/04* (2013.01)

(58) Field of Classification Search
    USPC ................ 351/158, 159.01, 159.02, 246, 247
    See application file for complete search history.

(56) References Cited

U.S. PATENT DOCUMENTS

| | | | |
|---|---|---|---|
| 3,958,560 | A | 5/1976 | March |
| 4,014,321 | A | 3/1977 | March |
| 4,055,378 | A | 10/1977 | Feneberg et al. |
| 4,122,942 | A | 10/1978 | Wolfson |
| 4,136,250 | A | 1/1979 | Mueller et al. |
| 4,143,949 | A | 3/1979 | Chen |
| 4,153,641 | A | 5/1979 | Deichert et al. |
| 4,214,014 | A | 7/1980 | Hofer et al. |
| 4,309,085 | A | 1/1982 | Morrison |
| 4,312,575 | A | 1/1982 | Peyman et al. |
| 4,401,371 | A | 8/1983 | Neefe |
| 4,463,149 | A | 7/1984 | Ellis |
| 4,555,372 | A | 11/1985 | Kunzler et al. |
| 4,604,479 | A | 8/1986 | Ellis |
| 4,632,844 | A | 12/1986 | Yanagihara et al. |
| 4,686,267 | A | 8/1987 | Ellis et al. |
| 4,740,533 | A | 4/1988 | Su et al. |
| 4,826,936 | A | 5/1989 | Ellis |

(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

(Continued)

*Primary Examiner* — Jack Dinh
(74) *Attorney, Agent, or Firm* — McDonnell Boehnen Hulbert & Berghoff LLP

(57) ABSTRACT

Systems for determining an individual's current focal plane by measuring parameters associated with binocular vision focusing using one or two contact lenses are provided. In an aspect, a system includes a first contact lens and a second contact lens respectively configured to be worn over first and second eyes of an individual. The first contact lens and the second contact lens respectively include first and second substrates, and first and second circuits respectively disposed on or within the first and second substrates and configured to respectively generate first data related to a focal trajectory of the first eye and second data related to a focal trajectory of the second eye, wherein the first circuit employs the second contact lens to generate the first data and the second circuit employs the first contact lens to generate the second data.

20 Claims, 16 Drawing Sheets

(56) References Cited

U.S. PATENT DOCUMENTS

| | | |
|---|---|---|
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,108,169 A | 4/1992 | Mandell |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicholson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder et al. |
| 2012/0109296 A1 | 5/2012 | Fan |
| 2012/0177576 A1 | 7/2012 | Hu |
| 2012/0201755 A1 | 8/2012 | Rozakis et al. |
| 2012/0245444 A1 | 9/2012 | Otis et al. |
| 2012/0259188 A1 | 10/2012 | Besling |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |

(56) References Cited

FOREIGN PATENT DOCUMENTS

| | | |
|---|---|---|
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems—II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Bionic contact lens 'to project emails before eyes,' http://www.kurzweilai.netforums/topic/bionic-contact-lens-to-project-emails-before-eyes, Last accessed Mar. 14, 2012, 2 pages.

Brahim, et al., "Polypyrrole-hydrogel composites for the construction of clinically important biosensors," 2002, Biosensors & Bioelectronics, pp. 53-59, vol. 17.

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.

"Contact Lenses: Look Into My Eyes," The Economist, Jun. 2, 2011, http://www.economist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3-μW CMOS Glucose Sensor for Wireless Contact-Lens Tear Glucose Monitoring," IEEE Journal of Solid-State Circuits, Jan. 2012, pp. 335-344, vol. 47, No. 1.

Liao, et al., "A 3-μW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.

Lingley, et al., "Multipurpose integrated active contact lenses," SPIE, 2009, 2 pages.

Liu, et al., "Miniature Amperometric Self-Powered Continuous Glucose Sensor with Linear Response," Analytical Chemistry, 2012, 7 pages.

Loncar, et al., "Design and Fabrication of Silicon Photonic Crystal Optical Waveguides," Journal of Lightwave Technology, Oct. 2000, pp. 1402-1411, vol. 18, No. 10.

Murdan, "Electro-responsive drug delivery from hydrogels," Journal of Controlled Release, 2003, pp. 1-17, vol. 92.

Pandey, et al., "A Fully Integrated RF-Powered Contact Lens With a Single Element Display," IEEE Transactions on Biomedical Circuits and Systems, Dec. 2010, pp. 454-461, vol. 4, No. 6.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Selner, et al., "Novel Contact Lens Electrode Array for Multi-electrode Electroretinography (meERG)," IEEE, 2011, 2 pages.

Singh, et al., "Novel Approaches in Formulation and Drug Delivery using Contact Lenses," Journal of Basic and Clinical Pharmacy, May 2011, pp. 87-101, vol. 2, Issue 2.

Thomas, et al., "Functional Contact Lenses for Remote Health Monitoring in Developing Countries," IEEE Global Humanitarian Technology Conference, 2011, pp. 212-217, IEEE Computer Society.

(56) References Cited

OTHER PUBLICATIONS

Tweedie, et al., "Contact creep compliance of viscoelastic materials via nanoindentation," J. Mater. Res., Jun. 2006, pp. 1576-1589, vol. 21, No. 2, Materials Research Society.

Wall, K., "Active contact lens that lets you see like the Terminator patented," Feb. 10, 2012, http://vvww.patexia.com/feed/active-contact-lens-that-lets-you-see-like-the-terminator-patented-2407, Last accessed Mar. 28, 2012, 5 pages.

Zarbin, et al., "Nanotechnology in ophthalmology," Can J Ophthalmol, 2010, pp. 457-476, vol. 45, No. 5.

INPUT DETECTION SYSTEM

TECHNICAL FIELD

This disclosure generally relates to determining an individual's current focal distance by measuring parameters associated with binocular vision focusing using one or two contact lenses.

BACKGROUND

Various virtual and augmented reality systems generate three dimensional images from a viewer's perspective. As the viewer's perspective changes, scaling and placement of objects of three dimensional images change. However, many of these systems are fixed focus and fail to accommodate the viewer's current focal distance to an object of the three dimensional image or the real world in which the three dimensional images are projected. Accordingly, these systems lack accuracy with respect to scaling and placement of objects of the three dimensional images.

DETAILED DESCRIPTION

Figure 1:
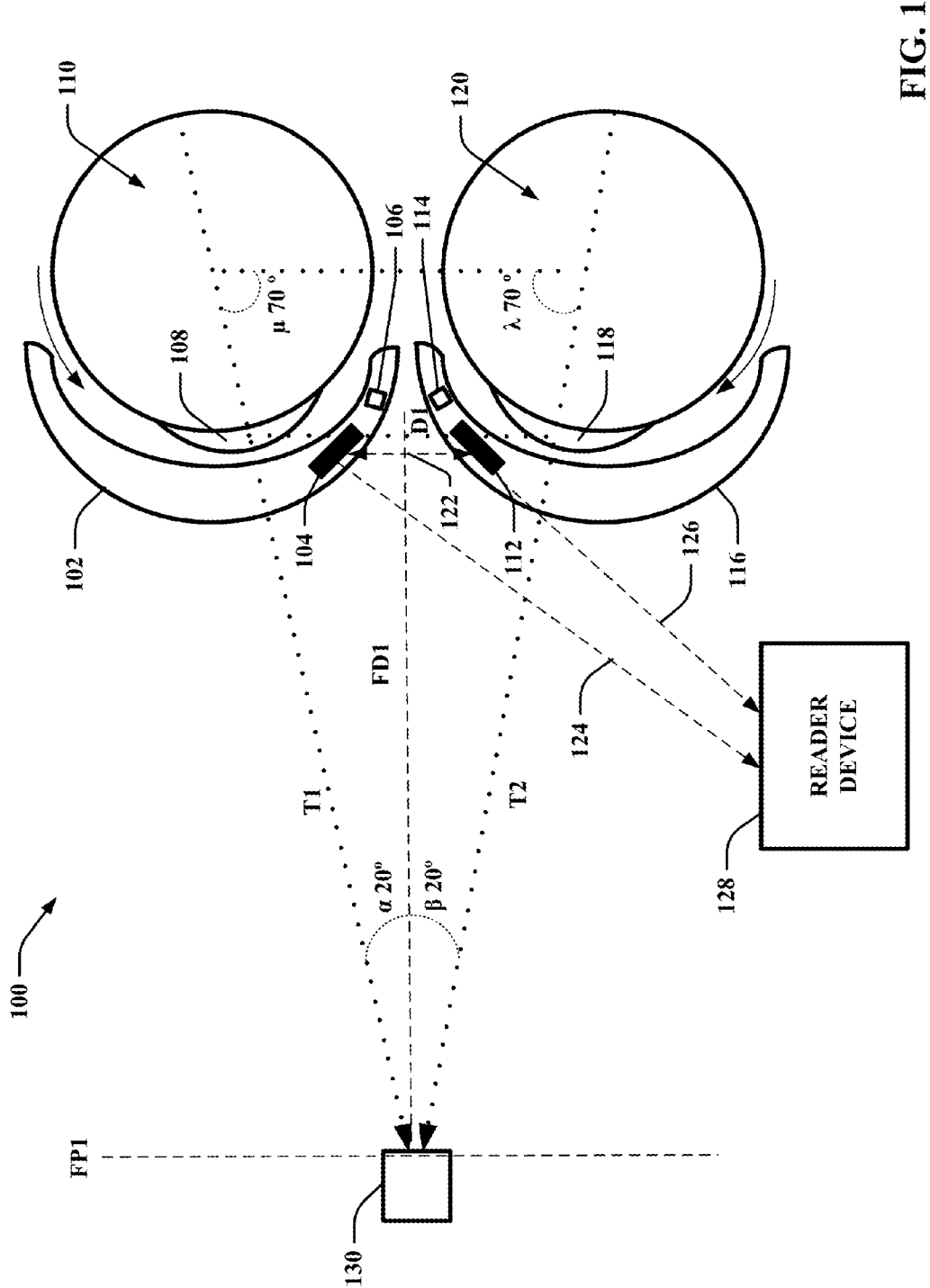
FIG. 1 presents an exemplary system for determining an individual's current focal distance using one or two contact lenses in accordance with aspects described herein

In one or more aspects, the disclosed subject matter relates to a system having a first contact lens and a second contact lens respectively configured to be worn over first and second eyes of an individual. The first and second contact lenses respectively have first and second substrates and first and second circuits respectively disposed on or within the first and second substrates. The first and second circuits are configured to respectively generate first data related to a focal trajectory of the first eye and second data related to a focal trajectory of the second eye. In an aspect, the first circuit employs the second contact lens to generate the first data and the second circuit employs the first contact lens to generate the second data. In another aspect, the first and second circuits are respectively configured to generate the first and second data respectively, in response to movement of the first and second eyes respectively, and particularly in response to vergence movement.

In another aspect, the disclosed subject matter provides contact lenses configured to generate data associated with a wearer's current focal distance. In an aspect, a contact lens is provided that is configured to be worn over a first eye of an individual. The contact lens comprises a substrate and a vergence component disposed on or within the substrate and configured to generate data related to movement of the first eye. The contact lens further comprises a communication component configured to receive, from a second contact lens worn over a second eye of the individual, second data related to movement of the second eye, and a processor configured to identify vergence movement of the first and second eyes based on the first and second data and determine a position of the first eye with respect to a position of the second eye based on the vergence movement.

In one or more additional aspects, a method is provided that includes generating first data related to position of a first eye over which a first contact lens is worn using the first contact lens, generating second data related to position of a second eye over which a second contact lens is worn using the second contact lens, transmitting the first data and the second data to a device remote from the first and second contact lenses. In an aspect, the method further includes detecting movement of the first eye and the second eye and generating the first data and the second data in response to the detecting.

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects. It should be appreciated that elements of the drawings, presented herein are not drawn to scale. Various features of objects/components presented in the drawings are exaggerated and/or simplified merely for exemplary purposes.

With reference now to the drawings, FIG. 1 presents an example embodiment of a system 100 for determining an individual's current focal distance using one or two contact lenses in accordance with aspects described herein. System 100 includes a pair of contact lenses 102 and 116 respectively worn over left 120 and right 110 eyes of an individual. System 100 presents a birds eye view (e.g. an elevated view from above) of the individual's eyes and the contact lenses worn over the eyes. In system 100, the individual to which eyes 110 and 120 belong is focused upon object 130. The system further includes a reader device 128 configured to wirelessly receive information from one or both contact lenses 102 and 116.

Contact lenses 102 and 116 each respectively include contact lens circuits 104 and 112 respectively, and vergence components 106 and 114, respectively, disposed on or within a substrate of the contact lenses. The respective vergence components 106 and 114 are communicatively coupled to the respective circuits 104 and 112, (e.g. via one or more wires). In an aspect, although the respective vergence components 106 and 114 are pictured as separate elements from the respective circuits 104 and 112, such illustration is merely provided for ease of description of the various functions of the different components. In particular, the vergence components 106 and 114 respectively connected to circuits 104 and 112 can form collective circuits on the respective contact lenses 102 and 116.

Vergence components 106 and 114 are configured to generate data associated with a wearer's current focal distance (FD) or focal plane (FP). In turn, a processor associated with contact lens 102, contact lens 116, and/or reader device 128, can employ the data to determine the wearer's current focal distance. Contact lens circuits 104 and 112 are configured to respectively facilitate generation of data by the respective vergence components, process data generated by the respective vergence components, and/or transmit data generated by the respective vergence components to external reader device 128.

As used herein, the term focal distance (FD) refers to distance an object upon which an individual (e.g. a wearer of contact lens 102 and/or 116) is gazing at is away from the individual. In an aspect, FD is measured as a substantially perpendicular trajectory path from a point between the eyes to an object upon which the individual is gazing. For example, in FIG. 1, dashed line FD1 (where FD1 is a variable) represents the individual's (to which eyes 110 and 120 belong) current FD with respect to object 130. Also, as used herein, the term focal plane (FP) refers to the plane in space located at the FD and substantially parallel to the eyes. For example, in FIG. 1, dashed line FP1 (where FP1 is a variable) represents the individual's current FP.

System 100 (and additional systems herein) employs properties of eye convergence/divergence to determine an individual's current FP and/or FD. Humans have binocular vision—with binocular vision, when an individual focuses on an object, the eyes undergo a process called accommodation. Accommodation is adjustment of optics of an eye to keep an object in focus on a retina as its distance from the eye varies. When a human with binocular vision looks at an object, the eyes must rotate around a vertical axis so that projection of the image is at the centre of the retina in both eyes. This rotational movement is referred to as vergence movement. In particular, as used herein, the term vergence movement includes inward or outward turning of both eyes in a substantially simultaneous fashion that occurs when focusing on an object. To look at an object relatively close to an individual, the eyes rotate towards each other. This process is referred to a convergence. While looking at an object farther away, the eyes rotate away from each other—this process is called divergence. When looking into the distance, the eyes diverge until parallel, effectively fixating the same point at infinity (or very far away).

Vergence movements are closely connected to accommodation of the eye. Under normal conditions, changing focus of the eyes to look at an object at a different distance will automatically cause vergence movement and accommodation. When an individual's eyes complete accommodation and vergence movement, the eyes will have brought an object gazed upon into focus. As used herein, the phrase the eyes have "reached convergence," is used to indicate that the eyes have performed vergence movement resulting in bringing of an object gazed upon into focus. In other words, the subject disclosure assumes eyes reach convergence when vergence movement associated with a focusing event is completed. Accordingly, the FD when the eyes have reached convergence is the individual's current FD.

In view of the above, system 100 employs vergence components 106 and/or 114 to generate data associated with vergence movement of the eyes 110/120 and more particularly, data representative of visual trajectory of the eyes 110 and 120 when the eyes have reached convergence. In turn, this movement data and/or visual trajectory data associated with vergence movement of the eyes can be employed to determine an individual current FD.

With reference to FIG. 1, T1 represents visual trajectory of eye 110 and T2 represents visual trajectory of eye 120 (where T1 and T2 are variables) when the eyes have reached convergence (e.g. focused upon) with respect to object 130. In order to focus on object 130, the eyes turn towards one another as can be discerned by angled position of respective corneas 108 and 118 of eyes 110 and 120. In turn, a processor associated with contact lens 102, contact lens 116, and/or reader device 128, can employ the visual trajectory data to determine the wearer's current FD or FP. For example, the visual trajectory data can include and/or represent, but is not limited to, at least one of: an intersection angle of T1 with FD1 (e.g. α 20°), an intersection angle of T2 with FD1 (e.g. β 20°), an intersection angle of T1 and T2 (e.g. α 20°+β 20°=40°), length of T1, length of T2, distance D1 (where D1 is a variable) between center (e.g. pupil or cornea 108 and 118 respectively) of the eyes, angle of an eye 110/120 with respect to a reference point, such as an axis of the eye 110/120 (e.g. angle μ 70° and/or angle λ 70°), position of the left eye, position of the right eye, or position of the left eye with respect to the right eye and vice versa. A processor can employ various algorithms and/or look up tables relating the various visual trajectory data parameters listed above with a FD and/or a FP to determine an individual's current FD and/or FP (e.g. FD1/FP1). For instance, the processor can employ various algorithms based on trigonometry principles.

A vergence component (e.g. 106 and/or 114) can employ various mechanisms in order to generate the above noted data related to an individual's FD. In an aspect, a vergence component employs one or more motion sensors to detect rotational motion of an eye with respect to a reference point. In another aspect, a vergence component can employ both a signal transmitting component and a signal receiving component. According to this aspect, the transmitting component of the first contact lens can transmit a first signal that is reflected off of the second eye or second contact lens and received back at the signal receiving component of the first contact lens. The vergence component (and/or a processor associated with the first contact lens or reader device) can then calculate time of flight information associated with the received reflected signal and employ the time of flight information to determine position of the first eye with respect to position of the second eye. In yet another aspect, each of the vergence components 106 and 114 can employ sensors or transmitters that communicate signals to one another where a feature of a respectively received signal is indicative of trajectory angle of the eye from which the signal was transmitted or a distance between a fixed reference point associated with the contact lenses or the eyes. The various mechanisms for generating data related to an individual's FD by a vergence component are discussed in greater detail with respect to FIGS. 3-8.

In an embodiment, system 100 uses information generated by both contact lenses 102 and 116 (e.g. via vergence component 106 and 114 respectively), in order to determine a wearer's current FD and/or FP. Further, in some embodiments, system 100 employs communication between contact lenses 102 and 116 in order for respective vergence component 106 and 114 to generate data that can be employed to determine a wearer's current FD and/or FP. In another embodiment, system 100 can operate with a single contact lens 102 or 116. According to this embodiment, the vergence component of the single contact lens can generate sufficient data that can be employed by either the single contact lens or an external device 128 to determine a wearer's current FD and/or FP. Accordingly, the operations and functions of contact lens circuits 104 and 112 respectively, and vergence components 106 and 114, respectively, can vary as described in greater detail with respect to FIG. 2.

In some aspects, in order to generate data related to an individual's FD or FP, contact lenses 110 and 120 communicate. For example, contact lens 110 can communicate information regarding its movement to contact lens 120 and vice versa. According to this aspect, circuits 104 and 112 can respectively include communication components (not shown) configured to transmit and receive information 122 between one another. In another aspect, circuit 104 can include a communication component to facilitate transmission of information from contact lens 102 to a reader device 128. For example, in an aspect, contact lens 102 can generate data related to a wearer's current FD and transmit the data to an external reader device 128 for processing and determination of the wearer's current FD based on the data. Similarly circuit 112 can include a communication component to facilitate transmission of information from contact lens 116 to a reader device 128.

Contact lenses disclosed herein, including contact lenses 102 and 116, can include a substrate that can include various materials. In an aspect, contact lenses disclosed herein include soft lenses made from one or more soft polymer materials including but not limited to, hydrogel, silicone based hydrogel, polyacrlyamide, or hydrophilic polymer. For example, in an aspect, contact lenses disclosed herein can include crosslinked hydrogels including hydrophilic monomers (e.g. N-Vinylpyrrolidone, 1-Ethenyl-2-pyrrolidone,N, N-dimethylacrylamide, 2-hydroxyethyl methacrylate, hydroxyethyl acrylate, methacrylic acid and acrylic acid), strengthening agents, ultraviolet light (UV) blockers, and tints. In another aspect, contact lenses disclosed herein can include silicone hydrogels (e.g. crosslinked hydrogels containing silicone macromers and monomers, as well as hydrophilic monomers that absorb water). In yet another aspect, contact lenses disclosed herein include hard lenses made from one or more rigid materials including but not limited to, silicone polymer, polymethyl methacrylate, or rigid gas permeable materials.

Turning now to FIGS. 2A-2D, presented are various embodiments of systems for determining an individual's current FD using one or two contact lenses in accordance with aspects described herein. Contact lenses of the systems described in connection with FIGS. 2A-2D can include one or more of the structure and/or functionality of contact lenses 102 and 116 (and vice versa). Repetitive description of like elements employed in respective embodiments of systems and contact lenses described herein is omitted for sake of brevity.

Figure 2A:
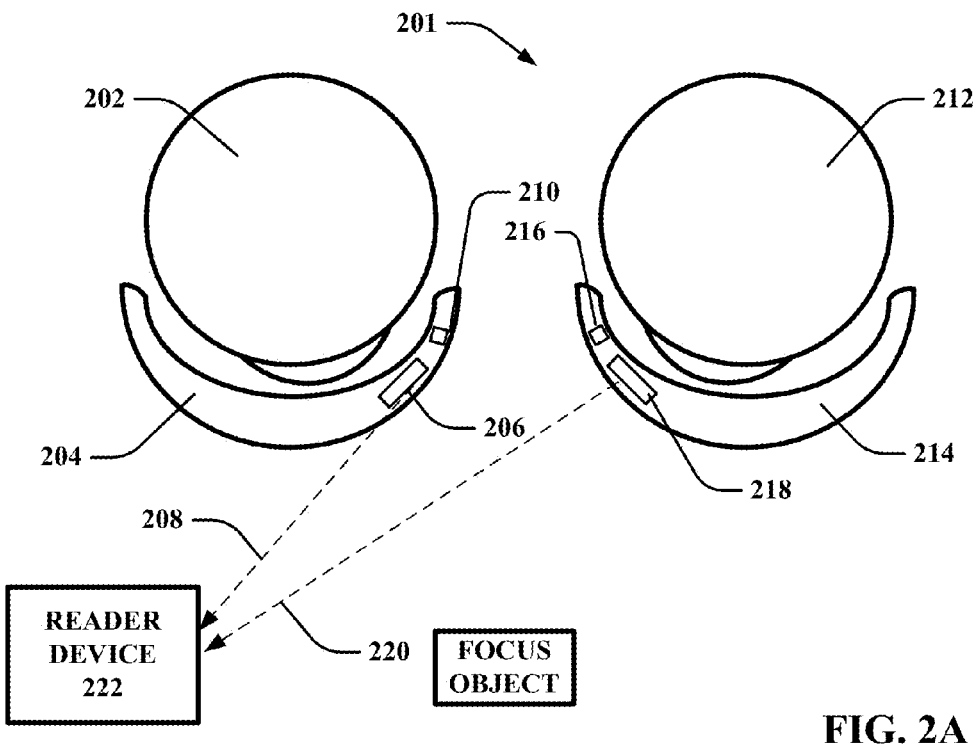
FIG. 2A-2D illustrate various systems for determining an individual's current focal distance using one or two contact lenses in accordance with aspects described herein

With reference initially to FIG. 2A, presented is an example system 201 for determining an individual's current FD. System 201 includes two contact lenses 204 and 214 respectively worn over an individual's eyes 202 and 212, and a reader device 222. Each of the contact lenses 204 and 214 include vergence components 210 and 216 respectively, and contact lens circuits 206 and 218 respectively. With system 201, contact lenses 204 and 214 each autonomously generate data related to a wearer's current FD/FP using respective vergence components 210 and 216. In other words, in system 201, contact lenses 204 and 214 do not need to communicate with one another to generate data related to a wearer's current FD/FP.

In response to generating the data related to the wearer's current FD/FP, the contact lenses 204 and 214 then respectively transmit the data 208 and 220 via communication components within respective circuits 206 and 218, to reader device 222 for processing thereof. According to this example system, the circuits 206 and 218 of contact lenses 204 and 214 do not need to perform deterministic processing relating generated data to various factors indicative of the wearer's current FD. Rather, reader device 222 performs this processing of the generated data. In particular, reader device 222 is configured to determine the individual's FP based on data received from both contact lenses 204 and 214.

In system 201, vergence components 210 and 216 are configured to perform various active functions to generate the data 208 and 220 related to the wearer's current focal distance (FD) or focal plane (FP). The various mechanisms for generating the data are discussed infra.

In an aspect, vergence components 210 and 216 respectively generate the data in response to respective movement of the eyes 202 and 212. According to this aspect, vergence components 210 and 216 are respectively configured to generate data related to at least movement of the eyes 202 and 212. For example, a vergence component (210 and/or 216) can generate data indicating direction and timing/speed of movement of an eye (202 and/or 212 respectively). According to this example, a processor associated with reader device 222 can employ this data to determine whether eyes 202 and 212 are performing vergence movement (e.g. converging or diverging) and thus changing FD, initiation of vergence movement, and completion of vergence movement (e.g. reaching convergence of the eyes).

In an aspect, a vergence component (210 and/or 216) can further generate data related to position of an eye (e.g. eye 202 and/or eye 212 respectively) with respect to a reference point, including position of the left eye 212 with respect to the right eye 202, and vice versa. For example, vergence component 210 can generate data that represents an angle parameter of eye 202 with respect to a reference point (e.g. an axis of the eye 202, or a reference point on the contact lens 204). Similarly vergence component 212 can generate data that represents an angle parameter of eye 212 with respect to a reference point.

Both contact lenses 204 and 214 can respectively transmit generated data 208 and 220, including data indicating changing positions of eyes 202 and 212 as they move over time, to reader device. Reader device 222 can then employ the data to determine the wearer's current FP. For example, a processor of reader device 222 can employ this data to determine that the eyes are undergoing vergence movement (e.g. because based on the data, it can be determined that both eyes are moving inward or outward at substantially a same time). The processor can further determine visual trajectory of eyes 202 and 212 respectively at initiation of vergence movement and completion of the vergence movement (e.g. by relating positions of an eye to predetermined visual trajectories). The processor can further determine the wearer's current FP at initiation of vergence movement and completion of vergence movement based on respective projected intersection points of visual trajectories of eyes 202 and 212.

Figure 2B:
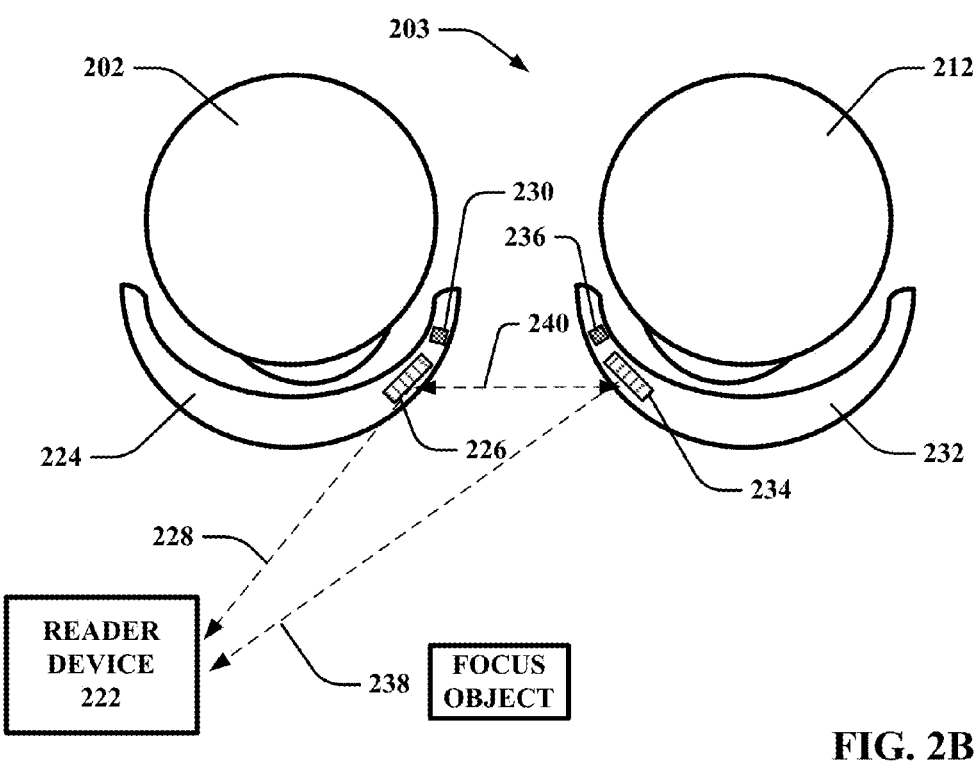

With reference now to FIG. 2B, presented is an example system 203 for determining an individual's current FD. In an aspect, system 203 can include at least the functionality and features of system 201. System 203 includes substantially the same components and features of system 201 with exception of vergence components 230 and 236 and circuits 226 and 234. In particular, the vergence components and circuits of contact lenses 224 and 232 include additional functionality and processing capabilities as compared to the vergence components and circuits of contact lenses 204 and 214.

In an aspect, with system 203, contact lenses 224 and 232 employ each other to generate data related to the wearer's current FD/FP using respective vergence components 230 and 236. For example, vergence component 230 can transmit signals to vergence component 236 which can be employed by circuit 234 to determine position of contact lens 232 and/or 224. Similarly, vergence component 236 can transmit signals to vergence component 230 which can be employed by circuit 226 to determine position of contact lens 232 and/or 224.

With system 203, circuits 226 and 234 can also communicate information 240 between one another to facilitate generating information indicative of the individual's FP. For example, vergence components 230 and 236 can include sensors configured to generate data representative of direction and timing of movement of the respective contact lenses. In an aspect, respective circuits 226 and 234 can be configured to transmit such movement data to one another via respective communication components of the circuits. In addition, the respective circuits 226 and 234 can further include processing capabilities, and employ the received movement data to determine when the eyes are performing vergence movement including initiation and stopping of vergence movement. In an aspect, in response to a determination that the eyes are undergoing vergence movements and/or have reached convergence, the respective vergence components 230/236 can initiate generation of additional data related to the wearer's current FP. For example, the respective vergence components can generate data related to position of the respective eyes 202/212 at completion of vergence movement, in response to completion of vergence movement.

In another example, circuits 226 and 234 can communicate information 240 between one another regarding operations of their respective associated vergence components. For example, vergence component 230 can transmit a signal at time T5 to vergence component 236 that is received at vergence component 236 at time T7. A communication component of circuit 226 can further communicate the transmit time, T5, to circuit 234. Accordingly, circuit 234 will have the transmit time and receipt time of the signal and can calculate time of flight information associated with the signal. Using additional properties of the transmitted signal and additional information related to spatial parameters of system 203 (e.g. frequency of the signal), circuit 234 (using a processor associated with the circuit) can perform processing of the signal to determine a position of contact lens 232 and/or relative positions of contact lens 224 and 232 with respect to one another.

In an aspect, any information generated/received by vergence components 230 and 236 can be transmitted to reader device for processing thereof. For example, rather than circuits 226 and 234 employing timing information of transmitted/received signals to determine time of flight information and/or respective positions of the respective contact lenses, the respective circuits can transmit such information to reader device 222 for such determinative processing.

Figure 2C:
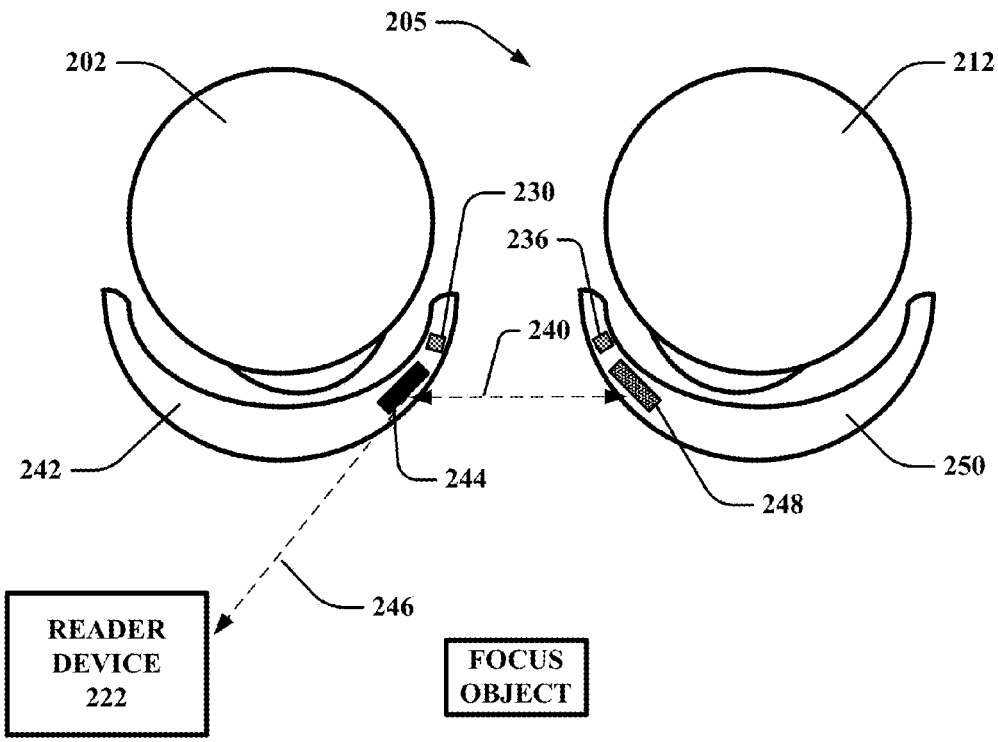

FIG. 2C, presents another example system 205 for determining an individual's current FD. In an aspect, system 205 can include same or similar functionality and features of system 203. System 205 includes substantially the same components and features of system 203 with the exception of circuits 244 and 248. In particular, circuit 244 includes additional functionality as compared to circuits 226 and 234 of contact lenses 224 and 232 (e.g. the contact lenses of system 203) while circuit 248 includes reduced functionality as compared to circuits 226 and 234 of the contact lenses 224 and 232.

With system 205, one contact lens of the pair (e.g. however it can be either contact lens) includes circuit 244. Circuit 244 include a processor configured to perform processing regarding data generated by both vergence component 230 and 236. In particular, data generated by vergence component 230 and 236 is provided to circuit 244 for determining information related to the individual's FP. According to this embodiment, circuit 248 merely includes functionality to communicate data 240 generated by vergence component 236 to circuit 244 and/or receive operative commands from circuit 244. For example, circuit 244 can command vergence component 236, via circuit 248, to generate data related to the individual's FD. Circuit 248 does not include functionality to communicate with reader device 222. On the contrary, the heavy processing functions and remote device communication roles of system 205 are restricted to a single contact lens of the pair. In an aspect, via circuit 244, contact lens 242 and 250 operate in a server/client relationship where lens 242 is the server and lens 250 is the client.

For example, with system 205, circuit 244 can receive information regarding movement and position of both eyes 202 and 212 where circuit 248 communicates movement/position data of eye 212 to circuit 244. Circuit 244 can employ the movement data to determine whether the eyes are performing vergence movement and when the eyes have reach convergence. Circuit 244 can further calculate relative positions of the eyes 202 and 212 to one another using the movement/position data. In an aspect, circuit 244 can perform additional processing of the data to determine an FD of the individual. Circuit 244 can further communicate any received or determined information 246, including information generated by vergence component 230 and 236, to reader device 222 for processing thereof.

Figure 2D:
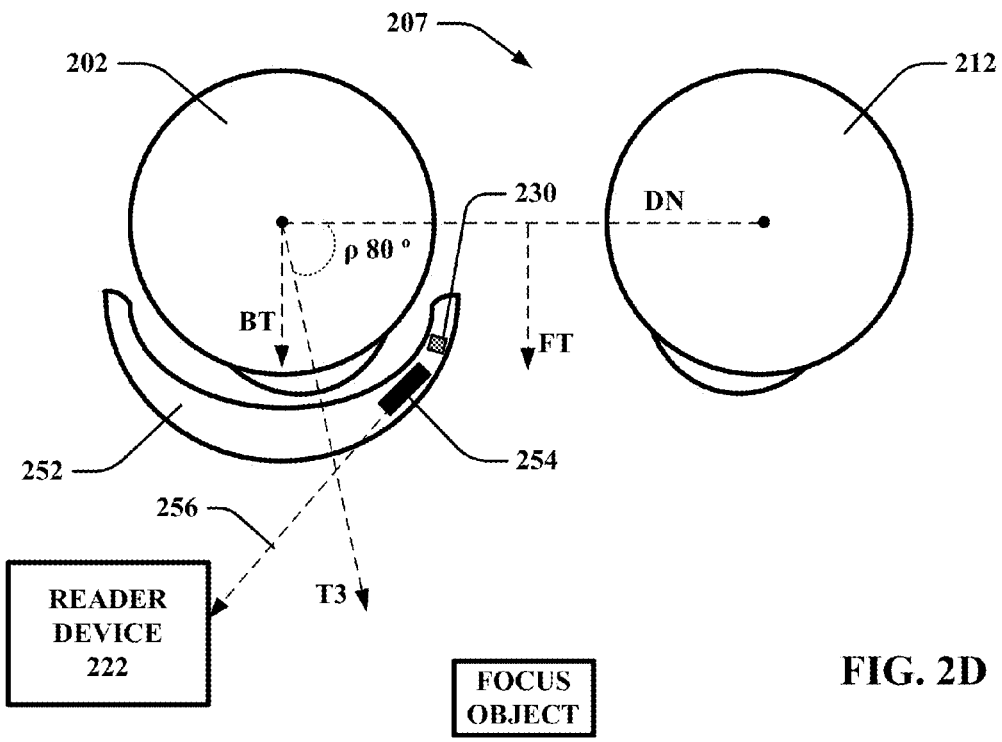

FIG. 2D, presents yet another example system 205 for determining an individual's current FD. Unlike systems 201, 203, and 205, system 207 includes a single contact lens 242. Contact lens 252 can include similar functionality of contact lens 242 with the exception that contact lens 252 does not communicate with a contact lens worn over 212 in order to generate information related to the individual's FD. On the contrary, contact lens 252 generates sufficient information regarding movement and position of eye 202 and/or eye 212 using vergence component 230 to facilitate determining the individuals FD. Circuit 254 can processes this information in the manner discussed above with respect to circuit 244 to determine the individual's current FD. Circuit 254 can also communicate generated or processed information 256 to reader device 222.

In an aspect, vergence component 230 generates information regarding movement of both eyes 202 and 204. According to this aspect, vergence component 230 can include means for determining movement of eye 212 when not wearing a contact lens. This mechanism is illustrated below with respect to FIG. 7.

However, in another embodiment, vergence component 230 only generates data regarding movement and position of eye 202. According to this aspect, a processor associated with circuit 254 and/or reader 222 is configured to determine an individual's FD based on movement and position data of a single eye 202. For example, the processor can employ various predetermined parameters regarding the spatial configurations of the eyes 202/212 and contact lens 252 as well as know properties of eye movement and/or various inferred parameters, in order to determine an individual's FD. For example, predetermined parameters can include a distance (DN, where DN is variable) between the center-points of eyes 202 and 212, a fixed imaginary trajectory FT (where FT is a variable) forming a 90° angle with DN and a fixed baseline trajectory BT (where BT is a variable) also forming a 90° angle with DN. In an aspect, the BT accounts for both eyes gazing away to a point at infinity (or very far away). At this point, both eyes 202 and 212 diverge until their respective visual trajectories are substantially parallel. With this embodiment, determination of the individual's FD can require a level of predication/inference regarding the visual trajectory of eye 212 with respect to the visual trajectory T3 (where T3 is a variable) of eye 202.

Figure 3:
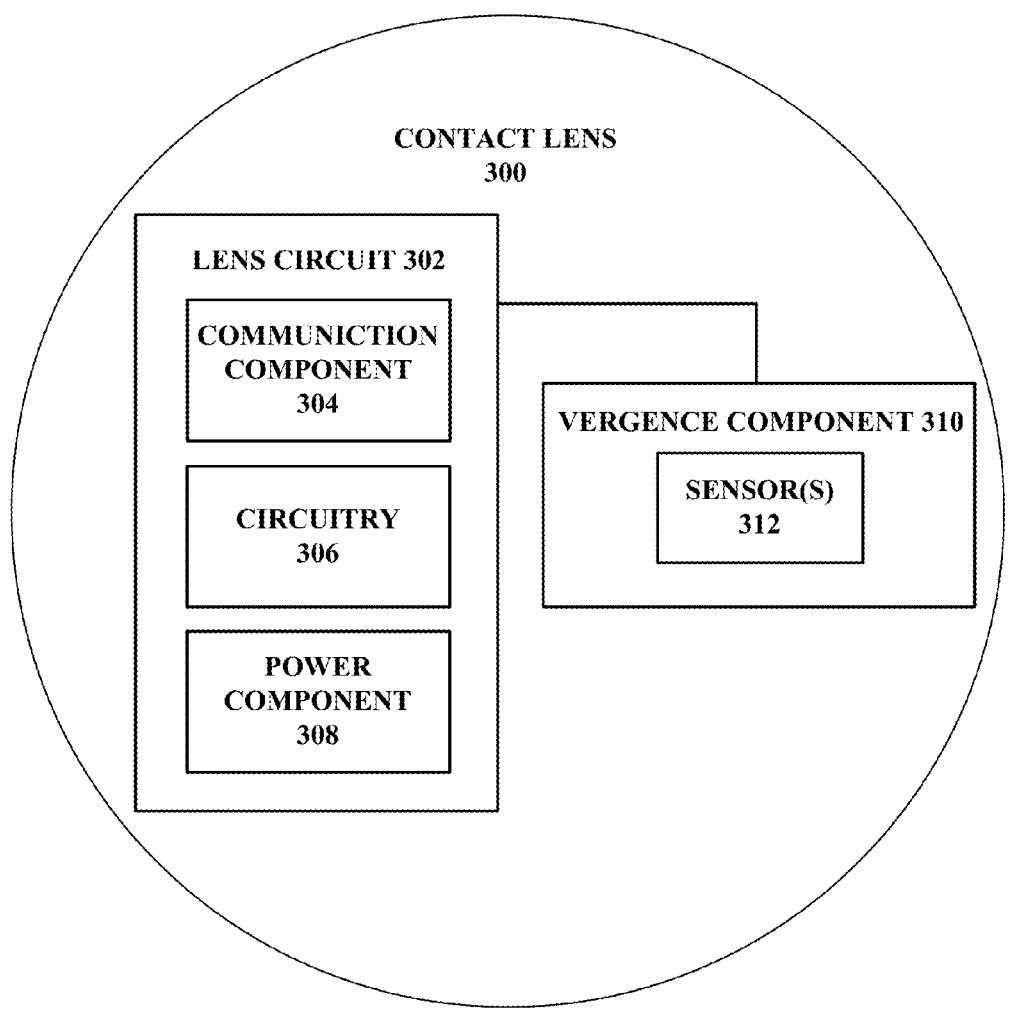
FIG. 3 presents an example embodiment of a contact lens that facilitates generating data related to a wearer's current focal distance in accordance with aspects described herein.

With reference on to FIG. 3, presented is a high level illustration of an example contact lens 300 configured to generate data indicative of a FD of a wearer of the contact lens in accordance with aspects described herein. Description of the functionality and operations of contact lens 300 is presented with the assumption that contact lens 300 is worn over one eye of an individual and performs sensing with respect to that eye and/or the other eye of the individual. However it should be appreciated that a contact lens 300 can be worn in both eyes of the individual. In various aspects, contact lens 300 can include one or more of the structure and/or functionality of contact lenses described with reference to the previous figures (and vice versa). Repetitive description of like elements employed in respective embodiments of contact lenses and contact lens circuits described herein is omitted for sake of brevity.

As shown in FIG. 3, contact lens 300 can include contact lens circuit 302 and vergence component 310 having at least one or more sensors 312. Contact lens circuit can include communication component 304, circuitry 306 and power component 308. In various embodiments, one or more of the lens circuit 302 including the communication component 304, circuitry 306, power component 308, and vergence component 310 including the one or more sensor 312, can be electrically or chemically coupled to one another to perform one or more functions of the contact lens 300. For example, one or more wires can connect the components of contact lens circuit 302 and one or more sensors of the vergence component 310.

Contact lens 300 employs vergence component 310 to generate data indicative of a FD of a wearer of contact lens 300. In particular, vergence component 310 employs one or more motion/positional sensors 312 to generate movement and positional data of one or both eyes of an individual wearing contact lens 300. Such positional data can be employed to determine whether the eyes are performing vergence movements, whether the eyes have reached convergence, visual trajectory of the eyes, and ultimately a FD or FP of the individual. In an aspect, vergence component 310 generates data, including positional data relating to a visual trajectory of an one or both eyes of an individual (e.g. data indicating a position of contact lens 300, a position of an eye over which contact lens 300 is worn, or a position of the other eye over contact lens 300 is not worn), in response to detected movement of an eye.

In an aspect, vergence component 310 employs one or more sensor(s) 312 disposed on or within a substrate of contact lens 300 to generate such movement and positional data including but not limited to: data related to movement of contact lens 300, data related to movement of an eye over which contact lens 300 is worn, data related to movement of the other eye of the individual (over which contact lens 300 is not worn) or data related to movement of another contact lens (e.g. a contact lens 300) worn over the other eye of the individual. In various aspects, the sensors 312 can generate movement data that accounts for a direction of movement (of an eye or contact lens) and timing of movement. For example, the one or more sensors can generate a signal indicating that the eye over which contact lens 300 is worn (or the other eye of the individual) is turning inward or outward at rate X, (where X is a variable).

In other aspects, the one or more sensors 312 can generate data related to a position of contact lens 300 or the eye over which contact lens 300 is worn, and/or a position of the other eye of the individual with respect to reference data, such as a reference point or reference position. For example, a reference point can include an axis of the eye over which contact lens 300 is worn or an axis of the other eye of the individual over which contact lens 300 is not worn. In another example, a reference position can include position of the eye over which contact lens 300 is worn when the individual is gazing at a point into infinity or far away. In yet another example, reference data can include distance between a pupil of the eye over which contact lens 300 is worn and the pupil of the other eye over which contact lens 300 is not worn when the eyes are gazing at a point into infinity or far away.

The one or more sensor(s) of vergence component 310 can include a variety of motion sensors, angle sensors, position sensors, and/or speed sensors. For example, one or more of the sensors can include but are not limited to: an accelerometer, an auxanometer, a capacitive displacement sensor, an inclinometer sensor, a gyroscopic sensor, a pressure sensor, piezoelectric sensor, a tilt sensor, or a triangulation sensor.

Contact lens 300 further includes contact lens circuit 302 to effectuate various electrical functions of the contact lens 300. Contact lens circuit 302 can include a communication component 304 to facilitate communication between two contact lenses respectively worn over the left and right eyes of an individual and/or to facilitate communication of information to an external device.

In aspect, communication component 304 can communicate data generated by vergence component 310 to an external device for processing of the data. For example, communication component 304 can wirelessly transmit data representative of positions of contact lens 300 or an eye over which contact lens 300 is worn when the eye initiates movement, positions during movement, and positions at the completion of movement. In another aspect, component 304 can communicate data generated by vergence component 310 to another contact lens worn over the other eye of the individual. For example, communication component 304 can transmit data relating to a direction of movement of contact lens 300 to the other contact lens. Further communication component 304 can receive data transmitted from another contact lens worn over the other eye of the individual, such as data relating to movement and/or a position of the other eye.

Accordingly, communication component 304 can include a receiver, a transmitter, a transceiver and/or a transducer. In an aspect, the communication component 304 includes a radio frequency (RF) antenna that transmits and receives data using a radio wave. In another aspect, the communication component can communicate using infrared (IR) antenna and or other light signals. In some aspects, communication component 304 employs circuitry to process signals received and/or signals transmitted. For example, circuitry 306 can include various hardware components including but not limited to a modulator/demodulator, a filter, an amplifier, and etc., to facilitate processing of signals generated by vergence component 310 and/or received from another contact lens.

Contact lens circuit 302 can additionally include circuitry 306 to facilitate functions of contact lens 102. For example, circuitry 306 can facilitate transfer of electrical signals and/or signals generated by vergence component 310 to the components of contact lens 300. Circuitry 306 can also include signal processing hardware and software, (e.g. amplifiers, modulators, and etc.) for processing of signals generated by vergence component 310 for wireless transmission thereof.

Further, contact lens circuit 302 can include a power source 308. Power source 308 can include any suitable power source that can provide necessary power for the operation of various components of the contact lens 300. For example, the power source 308 can include but is not limited to a battery, a capacitor, a solar power source, a mechanically derived power source (e.g., MEMs system), or an RF power source such as an RF power amplifier. In an aspect, contact lens circuit 302 does not require an onboard (e.g. on the contact lens 102) power source to operate. For example, contact lens circuit 303 can receive power via wireless energy transfer (e.g. using electromagnetic inductance techniques and related components).

Figure 4:
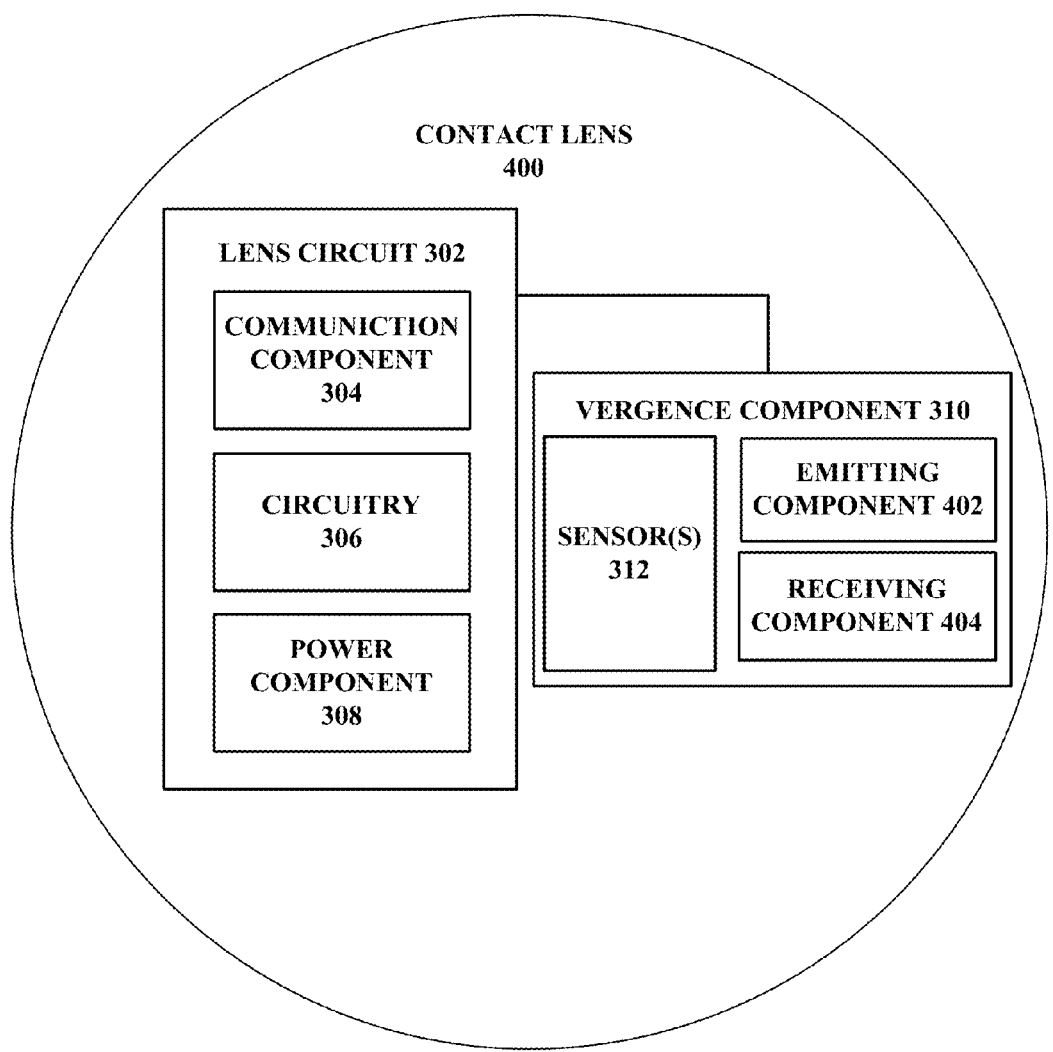
FIG. 4 presents another example embodiment of a contact lens that facilitates generating data related to a wearer's current focal distance in accordance with aspects described herein.

With reference now to FIG. 4, presented is a high level illustration of another example contact lens 400 configured to generate data indicative of FD of a wearer of the contact lens in accordance with aspects described herein. Description of the functionality and operations of contact lens 400 is presented with the assumption that contact lens 400 is worn over one eye of an individual and performs sensing with respect to that eye and/or the other eye of the individual. Repetitive description of like elements employed in respective embodiments of contact lenses and contact lens circuits described herein is omitted for sake of brevity.

In various aspects, contact lens 400 includes the components of contact lens 300 with addition of emitting component 402 and receiving component 404 to vergence component 310. Emitting component 402 and receiving component 404 provide mechanisms (e.g. additional to motion/position sensing) for generating data indicative of FD of a wearer of contact lens 400. Emitting component 402 is configured to transmit a signal away from contact lens 400 and towards the other eye of the individual and/or another contact lens worn over the other eye. In an aspect, emitting component 402 is configured to emit data in response to movement of the eye over which contact lens 400 is worn.

In some aspects, the transmitted signal is received at the other eye and/or the other contact lens and reflected off the other eye and/or the other contact lens respectively, back to receiving component 404 as a reflected signal. According to this aspect, transmit and receipt time of the transmitted/received signal can be detected by the transmitting component 402 and the receiving component 404 respectively. This information can further be employed to determine time of flight information associated with the transmitted/reflected signal which in turn can be employed to determine position of the eye over which contact lens 400 is worn, position of the other eye, and or position of both eyes with respect to one another.

In another embodiment, the transmitted signal is received by a receiving component (e.g. a receiving component 404 of a vergence component of the other contact lens) at another contact lens worn over the other eye. Similarly, receiving component 404 of contact lens 400 can receive a transmitted signal from an emitting component of the other contact lens. In accordance with this embodiment, transmit and receipt time of transmitted and received signals can be detected by the emitting components and receiving components of the respective contact lenses. For example, contact lens 400 can generate data indicating a transmit time of a signal it transmits to the other contact lens and generate data indicating a receipt time of a signal received from the other contact lens.

The contact lenses (e.g. contact lens 400 and the other contact lens) can further communicate these transmit/receipt times to one another (e.g. via communication component 304 and a communication component of the other contact lens). In another aspect, the contact lenses can communicate these transmit/receipt times to an external device for processing thereof (e.g. via communication component 304 and a communication component of the other contact lens). This information can further be employed to determine time of flight information associated with the transmitted/reflected signal which in turn can be employed to determine a position of the eye over which contact lens 400 is worn, a position of the other eye, and or a position of both eyes with respect to one another.

Also in accordance with this embodiment, the receiving component of the other device can generate data indicating a point or position at which a signal is received at the receiving component of the other device. For example, the receiving component can include a array of sensory array of signal detectors/receivers that can distinguish between point on the array where a signal is received. Similarly, receiving component 404 of contact lens 400 can include such an array and generate data indicating a point or position at which a signal is received from the other contact lens. Generated data relating to a point or position at which a signal is received by a receiving component can further be transmitted between contact lens circuits via respective communication components. This position data can also be employed to determine a position of the eye over which contact lens 400 is worn, a position of the other eye, and or a position of both eyes with respect to one another.

Signal emitting component 402 can emit/transmit various types of signals. In an aspect, the type of signal emitted by signal emitting component 402 is selected based on whether the signal is intended to be reflected off of the other eye, a particular component of the other eye, and/or another contact lens worn over the other eye. In another aspect, the type of signal emitted by the signal emitting component 402 is selected based on whether the signal is intended to be reflected back to receiving component 404 of contact lens 400 or received by a receiving component of the other contact lens.

In an aspect, the signal emitting component 402 emits radio waves. In another aspect, the signal emitting component emits microwave signals. According to these aspects, the signal emitting component 402 can include a transmitter that transmits pulses of radio waves or microwaves away from signal emitting component towards another contact lens worn of the individuals other eye, or the other. (e.g., an RF antenna, or a microwave antenna). Similarly, the signal receiving component 404 can include an appropriate receiver configured to receive radio signals and/or microwave signals. In an aspect, the signal receiving component 404 can include an array of sensors configured to detect a received RF or microwave signal. The sensor array can be configured to generate a signal indicating a point at which a signal is received at the array.

Further, where the signal emitting component 402 is configured to emit light signals the signal receiving component 404 can include an appropriate receiver configured to receive emitted light, such as one or more light detectors and/or photodetectors. In an aspect, the signal receiving component can include an array of light sensors or photodetectors. The array of light sensors/photodetectors can further be configured to generate a signal indicating a point at which a signal is received at the array.

Figure 5:
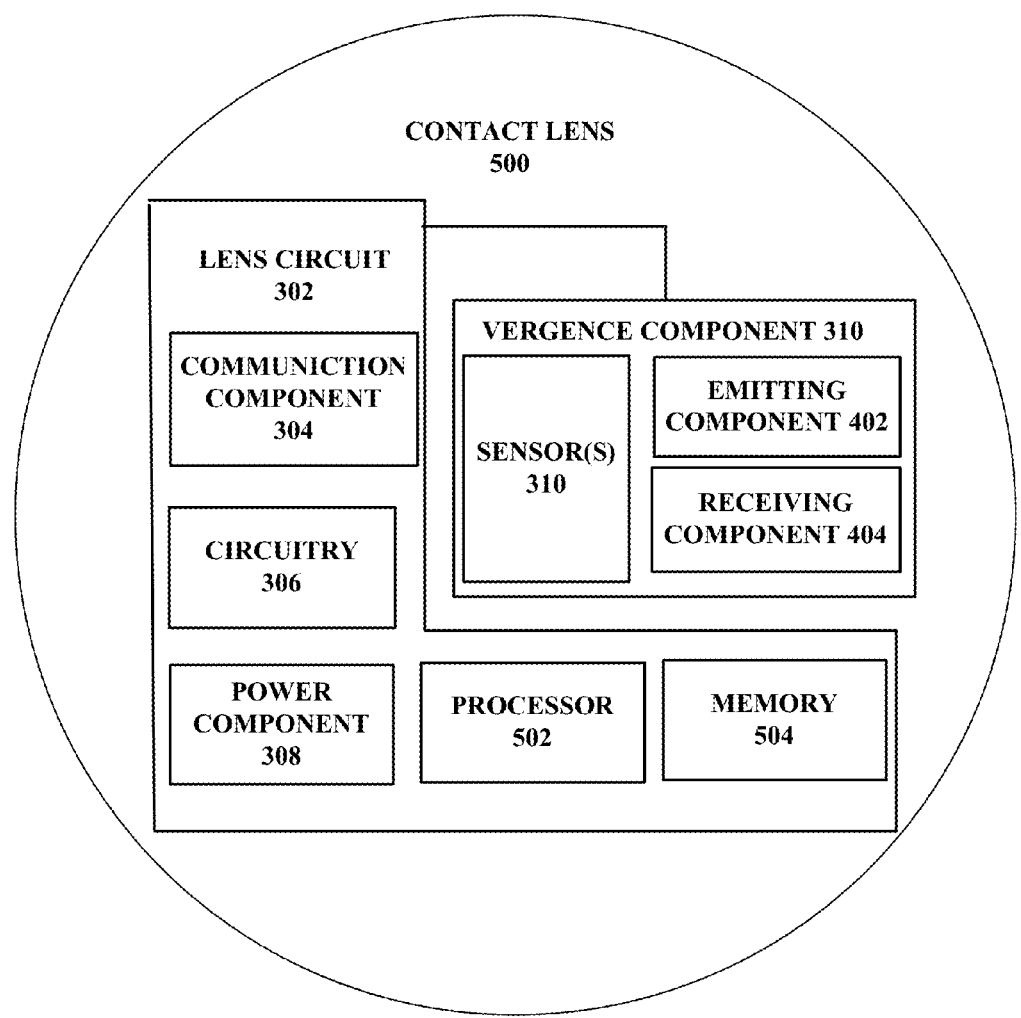
FIG. 5 presents another example embodiment of a contact lens that facilitates generating data related to a wearer's current focal distance in accordance with aspects described herein.

FIG. 5, presents a high level illustration of another example contact lens 500 configured to generate data indicative of a FD of a wearer of the contact lens in accordance with aspects described herein. Description of the functionality and operations of contact lens 500 is presented with the assumption that contact lens 500 is worn over one eye of an individual and performs sensing with respect to that eye and/or the other eye of the individual. Repetitive description of like elements employed in respective embodiments of contact lenses and contact lens circuits described herein is omitted for sake of brevity.

Contact lens 500 includes the components of contact lens 400 with the addition of processor 502 and/or memory 504 to contact lens circuit 302. In an embodiment, aspects of contact lens circuit 302 constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described. Contact lens circuit can include memory 504 for storing computer executable components and instructions. Processor 502 can facilitate operation of the computer executable components and instructions by contact lens circuit 504.

Processor 502 can be employed by contact lens 500 to perform various processing functions of contact lens 500 including but not limited to: processing associated with the generation of data by vergence component 310 and analysis of data generated by vergence component 310 and/or received at contact lens 500 by communication component 304 and/or receiving component 404. In particular, contact lenses 300 and 400 described above can be configured to perform minimal or no processing of such data. On the contrary, contact lenses 300 and 400 can transmit data to an external device or another contact lens for processing thereof. However, contact lens 500 is configured to perform various levels of processing of such data.

In an aspect, processor 502 performs full processing of data to determine an individual's current FD. In turn, determined/ inferred information representative of the individual's current FP can be transmitted by communication component 304 to an external device. For example, processor 502 can employ position data generated by vergence component representative of a position of the eye over which contact lens 500 is worn and a position of the other eye to determine visual trajectories of both eyes and ultimately determine a FD of the individuals based on a projected intersection point of the determined visual trajectories of both eyes. In turn, determined information representative of the individuals current FP can be transmitted by communication component 304 to an external device.

In another aspect, processor 502 can perform various levels of deterministic and/or inference based processing of data to generate intermediate data related to an individual's current FD. For example, processor 502 can process position information associated with the eye over which contact lens 500 is worn and the other eye of the individual to determine that both eyes are turning towards one another or away from one another (e.g. converging or diverging respectively), at substantially a same time. In other words, processor 502 can determine when the eyes of an individual are undergoing vergence movement, including the initiation of vergence movement and the completion of vergence movement.

Intermediate data can further be transmitted to an external device and/or another contact lens worn over the other eye of the individual, for additional processing thereof. Intermediate data can also be employed by contact lens 500 to facilitate operations of the contact lens 500. For example, in response to determining that the eyes of an individual are undergoing vergence movement, the processor 502 can initiate additional action by vergence component 310. For example, processor 502 can direct vergence component to generate data representative of a visual trajectory of the eye over which contact lens 500 is worn at a time when the vergence movement is completed (e.g. when the eyes have reached convergence).

In order to processes information generated by vergence component 310 and/or received at contact lens 500 from another contact lens worn over the other eye of the individual, such information can be stored permanently and/or temporarily in memory 504. For example, memory 504 can cache transmit and receipt times of a signals transmitted by emitting component 402 and reflected back to receiving component 404 in order to determine time of flight information. Memory 504 can further store various look-up tables and/or algorithms relating information generated by vergence component 310, and/or received at contact lens 500 from another contact lens worn over the other eye of the individual, to information associated with vergence movement and/or a focal distances.

For example, memory 504 can store look-up tables and/or algorithms that relate eye movement direction and speed to type of eye movement (converging or diverging eye movement), including initiation of vergence movement and completion of vergence movement. In another example, the algorithms and/or look-up tables can relate time of flight information associated with signals emitted by emitting component and signals received at receiving component to positions of one or both eyes. Similarly, the algorithms and/or look up tables can relate positions of receipt of signals at receiving component to positions of one or both eyes. Further, the algorithms and/or look-up tables can relate position of an eye and/or positions of both eyes to visual trajectory of the eye or both eyes and ultimately relate position/trajectory information to focal distance of the individual.

Memory 504 can further store additional predefined parameters associated with contact lens 500 and/or a system in which contact lens 500 is employed (e.g. system 100 and the like) useful for processing of information associated with determining an individual's FD. For example, memory 504 can store information related to the anatomy of the individual's eyes, such as distances between various components of the eyes. In another example, memory 504 can store baseline information representative of a position of the eyes when looking at a point into infinity or when looking at a point within less than about 75 mm from the individual.

In an embodiment, processor 502 can employ various (explicitly or implicitly trained) classification schemes or systems (e.g., support vector machines, neural networks, expert systems, Bayesian belief networks, fuzzy logic, data fusion engines, etc.) in connection with performing analysis of information generated by vergence component 310 and/or received at contact lens 500 from another contact lens worn over the other eye of the individual. A classifier can map an input attribute vector, x=(x1, x2, x3, x4 . . . , xn), to a confidence that the input belongs to a class, such as by f(x)=confidence(class). Such classification can employ a probabilistic or statistical-based analysis (e.g., factoring into the analysis utilities and costs) to prognose or infer a state of a retina. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used in this disclosure also is inclusive of statistical regression that is utilized to develop models of priority.

Figure 6B:
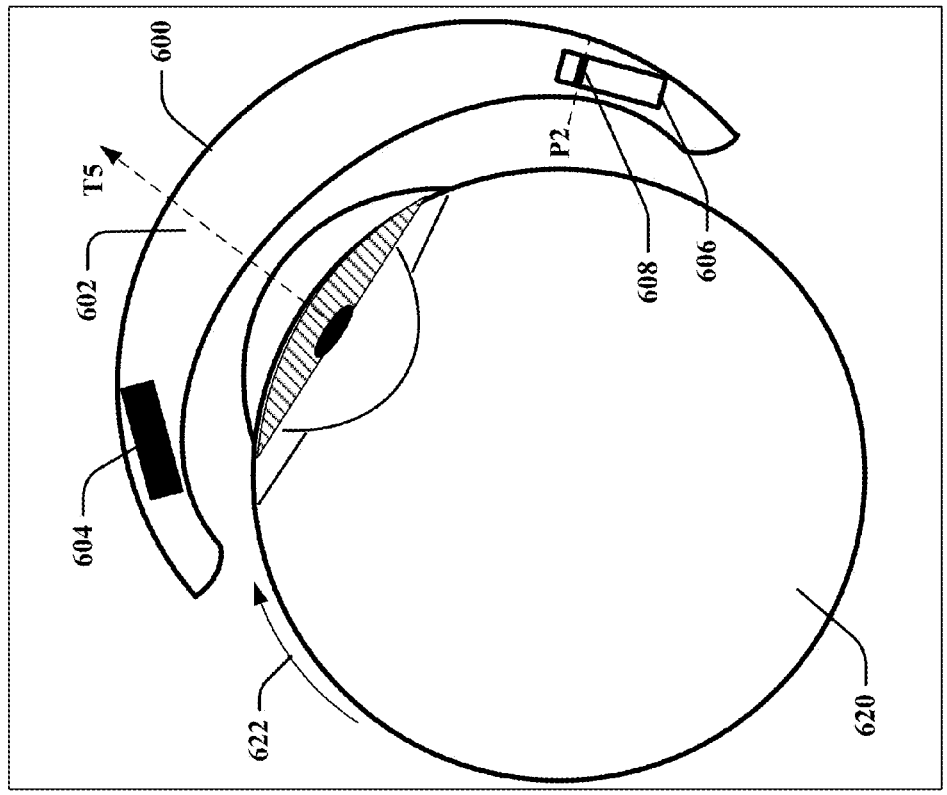
FIGS. 6A and 6B depicts example positions of a contact lens employing a motion/position sensor to generate data related to movement and/or a position of the contact lens as the eye over which the contact lens is worn changes focal distance, in accordance with aspects described herein.
Figure 6A:
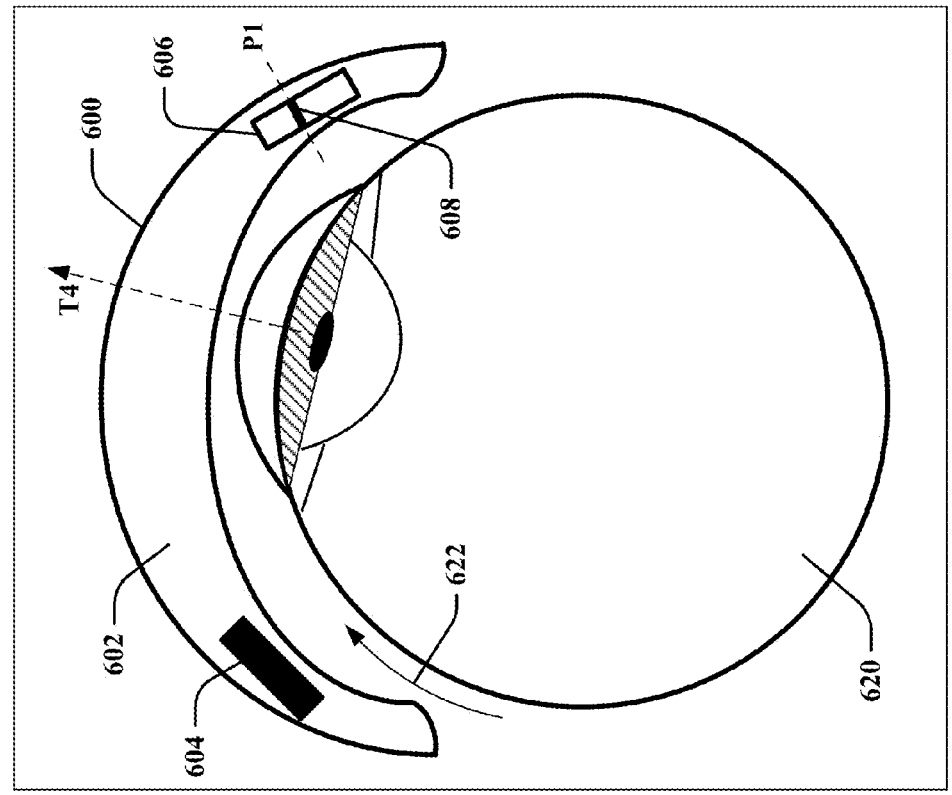

Referring now to FIGS. 6A and 6B, depicted are example embodiments of a contact lens 600 employing a motion/position sensor to generate data related to movement and/or a position of the contact lens as the eye over which the contact lens is worn changes FD. Repetitive description of like elements employed in respective embodiments of contact lenses and contact lens circuits described herein are omitted for sake of brevity.

FIGS. 6A and 6B depict contact lens 600 being worn over a left eye 620 of an individual. The contact lens includes a substrate 602. Located within the thickness of the substrate is a contact lens circuit and a vergence component 606. According to this embodiment, the vergence component 606 is a motion/position sensor having a component 608 configured to shift position in accordance with a shift in position of the eye 620. Although the vergence component 606 is presented as a single sensor, it should be appreciated that the vergence component can include any number N sensors.

For example, the eye 620 depicted in FIG. 6A has a first FD and the eye 620 depicted in FIG. 6B. Accordingly, the eye 620 depicted in FIG. 6A has a first visual trajectory T4 (where T4 is a variable), and the eye 620 depicted in FIG. 6B has a second visual trajectory T5 different from T4 (where T5 is a variable). In an aspect, the eye 620 changes focus from FIG. 6A to FIG. 6B, in part by performing vergence movement of the left eye 620 and right eye of the individual (not shown) and turning inward in the direction of arrow 622 toward one another until the eyes reach convergence.

In an aspect, motion/position sensor 606 is configured to detect at least movement of eye 620. In an aspect, motion/position sensor is further configured to detect speed and direction of movement of the eye. For example, shifting component 608 in FIG. 6A is located at a first position P1 while shifting component 608 of FIG. 6B is located at a second position P2 (where P1 and P2 are variables). Motions/position sensor 606 can detect position of the shifting component within the sensor as it moves with motion of the eye to determine direction of eye movement. For example, a shift from P1 to P2 can correspond to direction of movement of the eye. Further, motions/position sensor can detect speed at which the shifting component 608 moves within the sensor. The sensor 606 can further generate one or more signals corresponding to the detected motion/speed.

According to this aspect, it can be assumed that contact lens 602 moves with the eye as the eye moves. Further, although motion/position sensor is depicted as a rectangular box having limited dimensions for movement of the shifting component 608, it should be appreciated that such depiction is merely for exemplary purposes. In particular, motion sensor can have a dimension that substantially conforms to curvature of the eye 620, such as curved spherical shape, and that allows for movement of the shifting component in 360° and in various dimensions.

In an aspect, in addition to direction and speed of movement of the eye, motion sensor can generate data that can be processed to determine position of the eye 620 and/or trajectory T4 and T5 of the eye. For example, in an aspect, P1 and P2 can be associated with coordinate points. In an aspect, these coordinate points can be processed to determine position/trajectory of eye 620. In another aspect, contact lens 602 can employ two or more motion/position sensors 606 at different locations throughout the substrate and configured to have different shifting properties with respect to shifting component 608. According to this aspect, different coordinates can be generated by the respective sensors. These different coordinates can be combined and to determine a position/trajectory of eye 620. In some aspects, the coordinate points can be related to one or more predefined parameters or constants to facilitate processing. For example, a constant can include a position of the center point or axis of the eye 620. Using triangulation formulations and one or more baseline parameters (e.g. a trajectory/position of the eye when the eyes are looking at a point in infinity), a processor can determine FD of the individual.

Figure 7A:
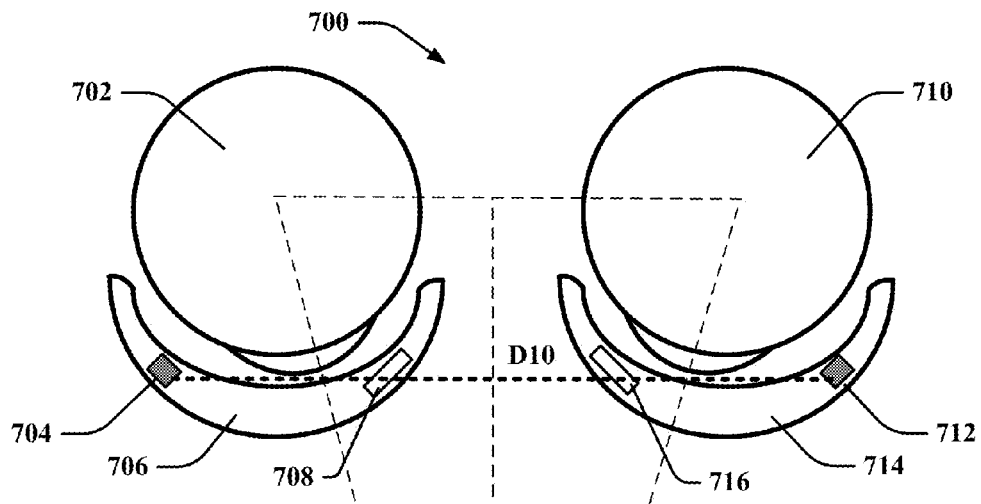
FIGS. 7A and 7B demonstrate a mechanism by which a pair of contact lenses facilitate determination of a wearer's current focal distance in accordance with aspects described herein.
Figure 7B:
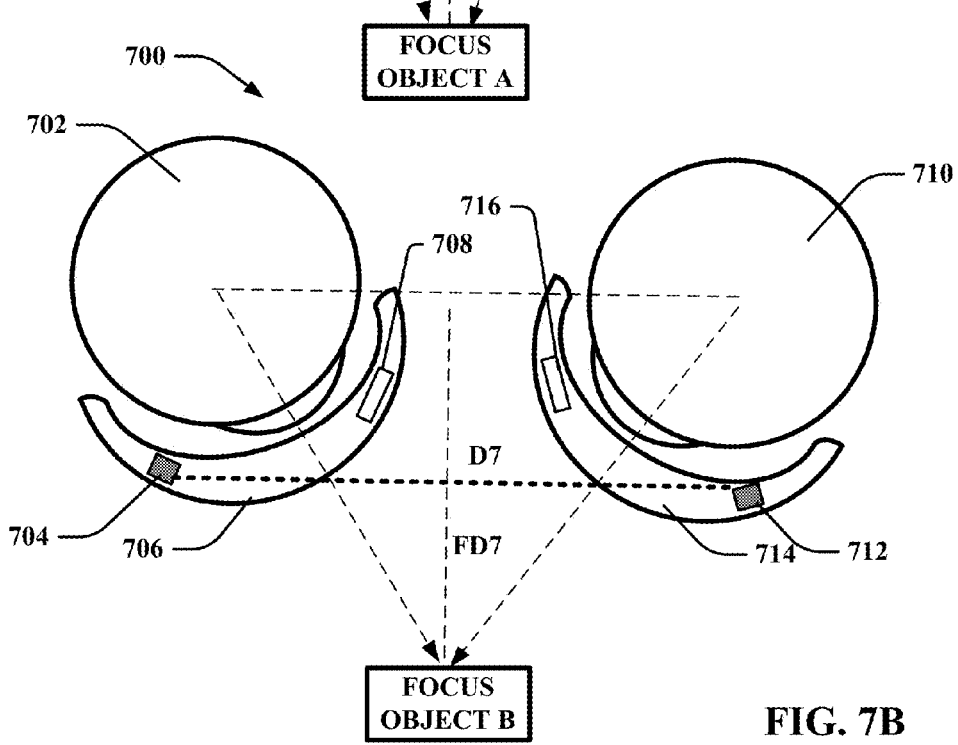

FIGS. 7A and 7B demonstrate an example embodiment of a system 700 employing a pair of contact lenses utilizing signal emitting and receiving components to detect position information associated with respective eyes of an individual. In particular, FIGS. 7A and 7B demonstrate a mechanism by which a pair of contact lenses facilitate determining a wearer's focal distance (FD) as the wearer changes focus. Repetitive description of like elements employed in respective embodiments of contact lenses and contact lens circuits described herein are omitted for sake of brevity.

System 700, as depicted in FIGS. 7A and 7B, is presented with two contact lenses 706 and 714 respectively worn over the right 702 and left 710 eyes of an individual. Contact lens 706 and 714 have respective substrates that includes respective contact lens circuits 708 and 716 and respective vergence component 704 and 712 disposed therein. The respective vergence component 704 and 712 include respective signal emitting components and a signal receiving components (not shown). In an aspect, although not depicted, contact lens 706 and/or contact lens 714 can further include one or more motion/position sensors (e.g. sensors 310).

The signal emitting components of the respective vergence components 704 and 712 are configured to emit signals to each other. For example, the signal emitting component of vergence component 704 can transmit a signal, such as an RF signal, to a signal receiving component of vergence component 712. Similarly, the signal emitting component of vergence component 712 can transmit an RF signal to a signal receiving component of vergence component 704. The respective vergence components can further communicate signal emit times and signal receipt time to one another (e.g. via a communication components disposed within respective circuits 708 and 716) or a remote device. Time of flight information for a particular signal can then be determined using the transmit and receipt times of the signal. This time of flight information can further be employed to determine a distance between the respective vergence components 704 and 712 which can further be correlated to a FD of the wearer.

For example, in FIG. 7A, an individual is focused upon focus object A and in FIG. 7B, the individual changes focus to focus object B. Focus object A is farther away from the individual with respect to focus object B. With reference to FIG. 7A, vergence components 704 and 712, are located at a fixed position within the substrates of contact lenses 706 and 14 respectively, and are a distance D10 apart, (where D10 is a variable). In an aspect, D10 is determined as a function of time of flight information for signals transmitted between the respective vergence components 704 and 712. D10 can further be employed to determine the individual's FD. For example, using various triangulation methods, D10 can be correlated to a focal distance of FD10.

With reference now to FIG. 7B, the individual shifts focus to a new object, focus object B. When shifting focus, eyes 702 and 710 as well as the contact lenses respectively worn over the eyes, contact lenses 706 and 714, turn substantially simultaneously inward towards one another. As a result, the distance between the fixed vergence components 704 and 712 respectively located on contact lenses 706 and 714 changes. In this example, the distance D7 (where D7 is an integer) becomes smaller. In an aspect, D7 is determined as a function of time of flight information for signals transmitted between the respective vergence components 704 and 712. D7 can further be employed to determine the individual's FD. For example, using various triangulation methods, D7 can be correlated to a focal distance of FD7.

Figure 8:
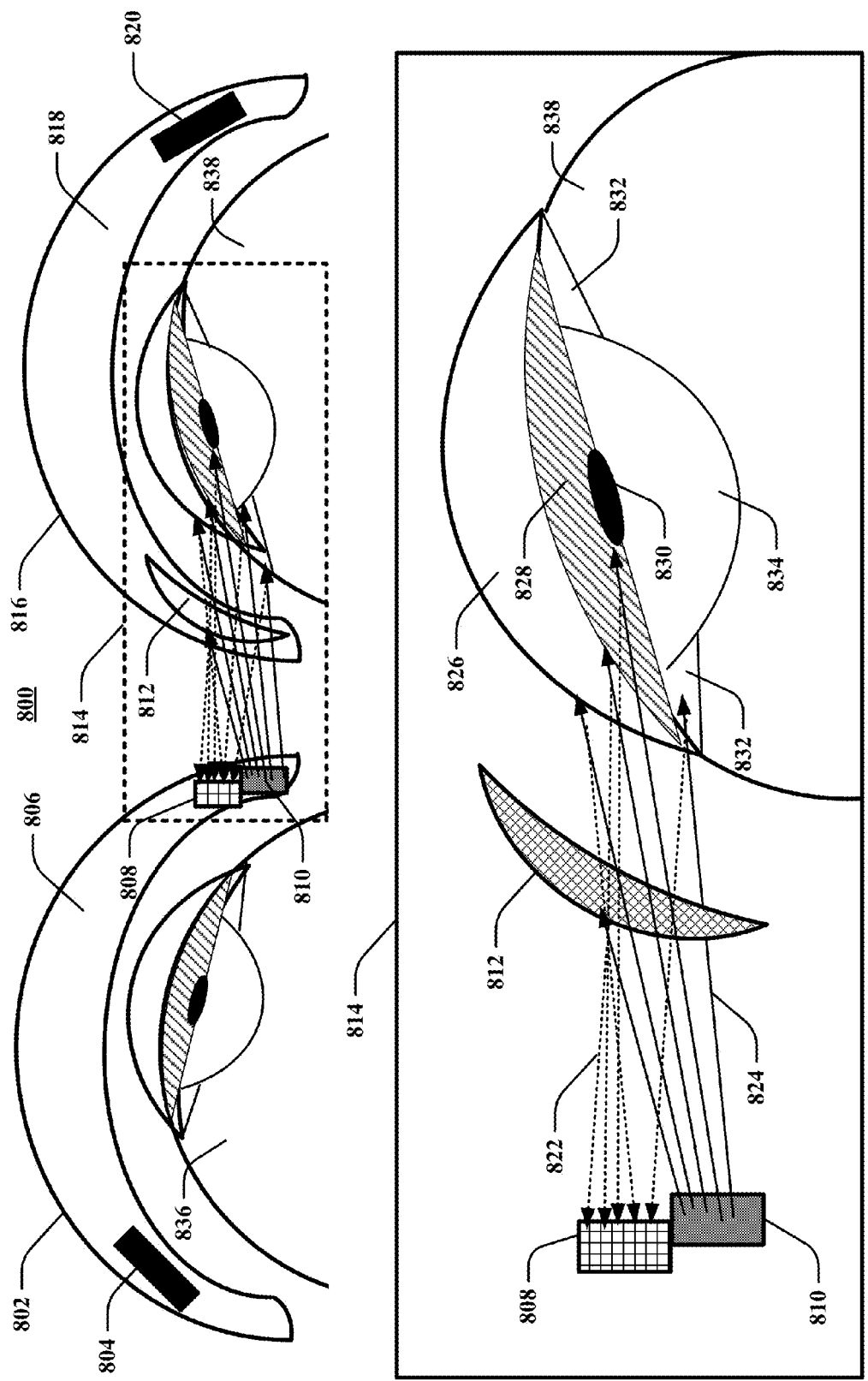
FIG. 8 demonstrates an example embodiment of a system employing a contact lens utilizing signal emitting and receiving components to detect position information associated with respective eyes of an individual, in accordance with aspects described herein.

FIG. 8 demonstrates an example embodiment of a system 800 employing a contact lens utilizing signal emitting and receiving components to detect position information associated with respective eyes of an individual. Repetitive description of like elements employed in respective embodiments of contact lenses and contact lens circuits described herein are omitted for sake of brevity.

System 800 is presented with two contact lenses 802 and 816 respectively worn over the left 836 and right 838 eyes of an individual. Contact lens 802 has a substrate 806 that includes a contact lens circuit 804 and a vergence component disposed therein. The vergence component includes an emitting component 810 and a receiving component 808. In an aspect, although not depicted, contact lens 802 can further include one or more motion/position sensors (e.g. sensors 310). The signal emitting component 810 is configured to emit signals towards the right eye 838 and/or contact lens 816 worn over the right eye 838. These signals are intended to reflect off they eye and/or the contact lens 816 respectively, back to receiving component 808 of contact lens 802.

In an aspect, contact lens 816 can include a signal reflection component 812 located within a substrate thereof. This signal reflection component 812 can include a material configured to reflect signals transmitted by transmitting component 810. According to this aspect, signal emitting component 810 can be configured to emit signals towards signal reflection component 812. Contact lens 816 can also include a contact lens circuit 820 located within the substrate 818.

The signal refection component 812 can be fixed within the substrate 818 and move with the contact lens as the eye 838 moves. (System 800 assumes that the contact lenses 802 and 816 move with the eyes as the eyes move). The signal reflection component 812 can further have a shape that results in reflection of a signal at a particular trajectory depending on where an emitted signal hits the signal reflection component 812. According to this aspect, as the angle/position of the signal reflection component changes with the movement of the contact lens, the point at which a signal is reflected off of the signal reflection component 812 changes, and thus the trajectory of the reflect signal changes.

In an aspect, the signal emitting/receiving components of contact lens 802 can generate data indicating a transmit/receipt time of a transmitted/reflected signal. It should be appreciated that the transmit/receipt time will be a function of the point at where an emitted signal is intercepted and the trajectory distance of the emitted signal and reflected signal. This transmit/receipt time can be employed to determine time of flight information associated with the signal which in turn can be employed to determine a position of eye 836, a position of eye 838 and/or a position of both eyes with respect to one another. This position information can further be employed to determine a FD of the individual.

Box 814 presents an enlarged portion of system 800. As seen in box 814, eye 838 is presented with various physical features. In particular, a human eye 838 includes a cornea 826, an iris 828 disposed between ciliary muscles 832, a pupil 830 and a lens 834. One or more of these features of the eye 838 move with the eye as the eye changes focus using vergence movements. In an aspect, signal emitting component 810 is configured to emit a signal 824 (represented by the solid lines) towards one or more of these physical features of the eye which is reflected back from the respective features as a reflected signal 822 (one or more of the dashed lines) and received at receiving component 808. According to this aspect, system 100 can generate time of flight data related to a position of eye 836 and/or eye 838 without requiring a contact lens to be worn over eye 838. In an aspect, the signal emitting component can emit a different type of signal (e.g. a radio signal vs. a light signal and/or light signals of various wavelength) depending on the intended physiological receiving feature. Further, properties of the receiving feature (e.g. location, shape, absorbance parameters), can be employed to facilitate determining time of flight information and/or correlating the time of flight information to a FD of the individual.

Also as shown in box 814, signal emitting component 810 can emit a signal 822 towards signal reflection component 812 of contact lens 816. (In an aspect, signal emitting component 810 can emit a signal to the substrate of contact lens 816 where the substrate does not include signal reflection component 812). An emitted signal 822 can be reflected off signal reflection component 812 and received at signal receiving component 808.

In an aspect, in addition to determining time of flight information associated with a transmitted/reflected signal, position of receipt of a reflected signal at the signal receiving component 808 can also be determined. This receipt position can further indicate position of eye 836, eye 838, and/or position of eye 836 with respect to eye 838, which in turn can be employed to determine FD of the individual. For example, receiving component 808 can include an array of sensors configured to generate a signal corresponding to receipt of the reflected signal. Each of the sensors in the array can be associated with location information, such as a coordinate of a coordinate system. Accordingly, a coordinate of a received signal at receiving component 808 can be determined depending on the particular sensor of the array at which a signal is received.

Figure 9:
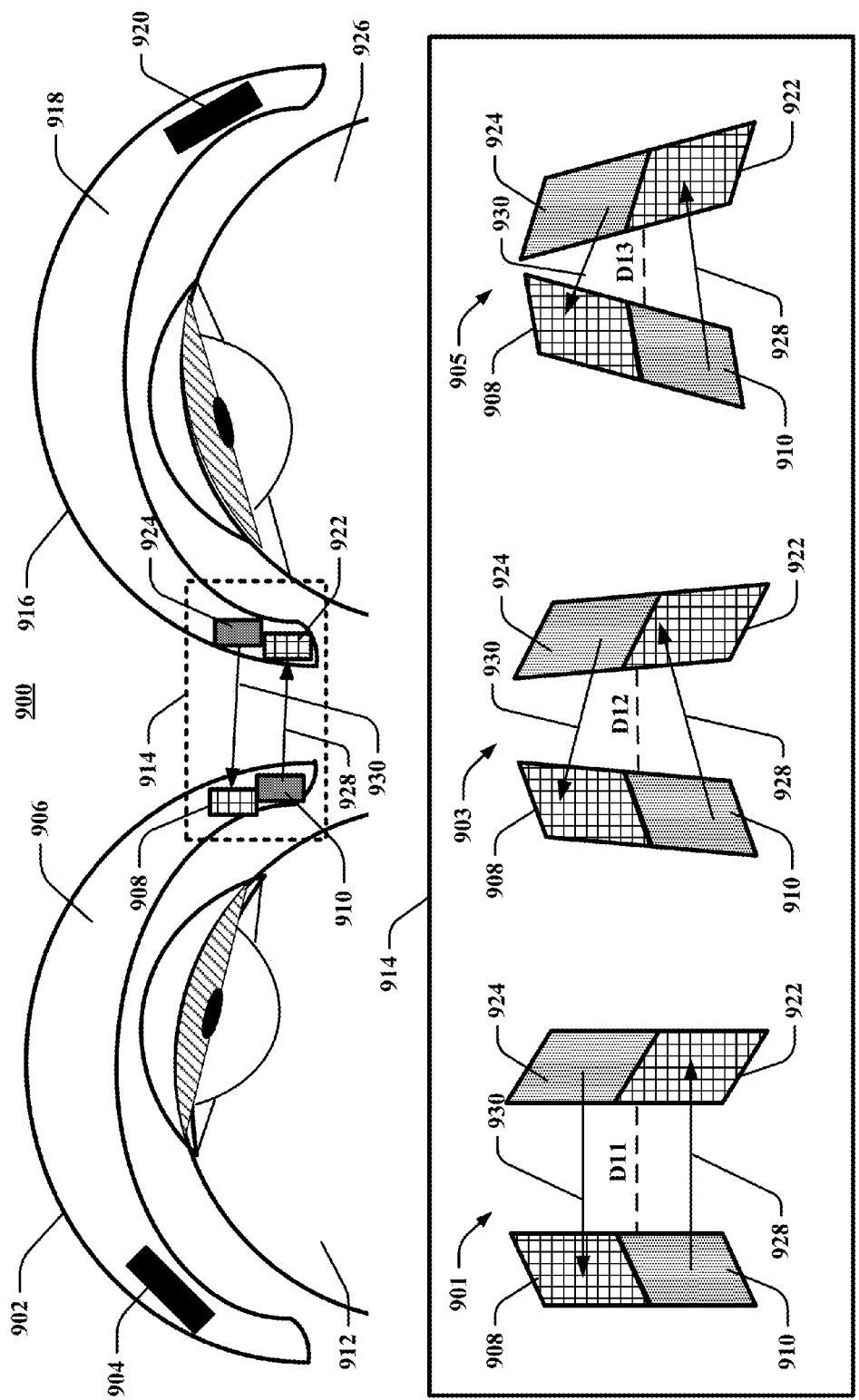
FIG. 9 demonstrates an example embodiment of a system employing a pair of contact lenses utilizing signal emitting and receiving components to detect position information associated with respective eyes of an individual, in accordance with aspects described herein.

FIG. 9 demonstrates an example embodiment of a system employing a pair of contact lenses utilizing signal emitting and receiving components to detect position information associated with respective eyes of an individual. Repetitive description of like elements employed in respective embodiments of contact lenses and contact lens circuits described herein is omitted for sake of brevity.

System 900 employs intercommunication of information generated by respective vergence components of respective contact lenses 902 and 916 worn over the left and right eyes of the individual. According to this embodiment, vergence components of each of the respective contact lenses 902 and 916 include a signal emitting component and a signal receiving component disposed within respective substrates 906 and 918 of the respective contact lenses. For example, the vergence component of contact lens 902 includes signal emitting component 910 and signal receiving component 908. The vergence component of contact lens 916 includes signal emitting component 922 and signal receiving component 224. In an aspect, although not depicted, the respective vergence components can further include one or more motion/position sensors (e.g. sensors 310).

Signal emitting component 910 is configured to emit a signal that is received at signal receiving component 922. A communication component associated with circuit 920 is configured to transmit information pertaining to a received signal at signal receiving component 922 to at least one of contact lens 902 or an external device. This information can include a location/position of a received signal and a time of receipt. Further, a communication component associated with circuit 904 can transmit information indicative of a transmit time of a signal to contact lens 916 and/or an external device.

Similarly, signal emitting component 924 is configured to emit a signal that is received at signal receiving component 908. A communication component associated with circuit 904 is configured to transmit information pertaining to a received signal at signal receiving component 908 to at least one of contact lens 916 or the external device. This information can include location/position of a received signal and time of receipt. A communication component associated with circuit 922 can also transmit information indicative of a transmit time of a signal to contact lens 902 and/or an external device.

In an aspect, the signal emitting components 910 and 924 can be configured to emit signals at a same or substantially same time using communications between the contact lenses via circuits 904 and 920. Generated, transmitted and/or received information pertaining to location of a received signal, transmit time of the signal, and/or receipt time of a signal can be processed to determine a FD of the individual.

Signal receiving components 908 and 922 includes a material configured to identify a point at which a signal is received at the material. For example, signal receiving components 908 and 922 can include a sensor array where each sensor of the array is associated with a position or coordinate of a coordinate system. For example, the sensor array can include an array of RF receivers and/or an array of photodetectors. In another example, the material can include an electrically responsive material configured to determine a point where an electrical signal is received. According to this embodiment, signal emitting components 910 and 924 are configured to emit a signal to signal receiving components 908 and 922 respectively. The respective signal receiving components 909 and 922 are configured to determine position/location of a received signal which can be employed to determine position of eye 912, eye 926, and/or position of eye 912 with respect to eye 926, trajectory of eye 912 and/or eye 926, and ultimately FD of the individual.

Box 914 depicts an enlarged drawing of the signal emitting and receiving components of system 900. In particular, box 914 illustrates exemplary positions of respective signal receiving and emitting components of the respective contact lenses 902 and 916 as the eyes 912 and 926 converge. In an aspect, as the eyes converge, the respective vergence components (e.g. the combined signal emitting component and signal receiving component of a single contact lens) are become closer to one another and angled inward toward one another. Positions of vergence components with respect to one another is a direct reflection of position of the eyes 912 and 926 with respect to one another. Accordingly, position at which a signal is received at respective vergence components directly reflects position of the eyes with respect to one another and thus indirectly reflects respective trajectories of the eyes and FD of the individual.

As seen at position 901, the signal emitting components and signal receiving components are substantially parallel at a first distance D11 apart (where D11 is a variable). Signal emitting component 910 emits a signal 928 that is received at signal receiving component 922 at a first position. The first position at which the signal 928 is received at signal receiving component 922 is a function of distance D11 and angle between the signal emitting component 910 and the signal receiving component 922. Similarly, signal emitting component 924 emits a signal 930 that is received at signal receiving component 909 at a first position. The first position at which the signal 930 is received at signal receiving component 908 is a function of distance D11 and angle between the signal emitting component 924 and the signal receiving component 908. In an aspect, a processor associated with either circuit 904 and 920 or an external device, determines FD of the individual at least as a function of the first positions of received signals 929 and 930.

As seen at position 903, signal emitting components and signal receiving components are angled inward and located at a second distance D12 apart, (where D12 is a variable). In an aspect, at position 903, the eyes 912 and 926 have converged with respect to the eyes at position 901. Signal emitting component 910 emits a signal 928 that is received at signal receiving component 922 at a second position different than the first position. The second position at which the signal 928 is received at signal receiving component 922 is a function of distance D12 and angle between the signal emitting component 910 and the signal receiving component 922. Similarly, signal emitting component 924 emits a signal 930 that is received at signal receiving component 908 at a second position different than the first position. The second position at which the signal 930 is received at signal receiving component 908 is a function of distance D12 and angle between the signal emitting component 924 and the signal receiving component 908. In an aspect, a processor associated with either circuit 904 and 920 or an external device, determines FD of the individual at least as a function of the second positions of received signals 928 and 930.

As seen at position 905, signal emitting components and signal receiving components are angled even further inward and located at a third distance D13 apart, (where D13 is a variable). In an aspect, a position 903, the eyes 912 and 926 have converged with respect to the eyes at position 901 and 903. Signal emitting component 910 emits a signal 928 that is received at signal receiving component 922 at a third position different than the first and second positions. The third position at which the signal 928 is received at signal receiving component 922 is a function of distance D13 and angle between the signal emitting component 910 and the signal receiving component 922. Similarly, signal emitting component 924 emits a signal 930 that is received at signal receiving component 908 at a third position different than the first and second positions. The third position at which the signal 930 is received at signal receiving component 908 is a function of distance D13 and angle between the signal emitting component 924 and the signal receiving component 908. In an aspect, a processor associated with either circuit 904 and 920 or an external device, determines FD of the individual at least as a function of the third positions of received signals 928 and 930.

Although, the signal emitting components and signal receiving components are depicted having a rectangular shape, it should be appreciated that such shape is provided merely for exemplary purposes. In particular, the signal emitting components and signal receiving components can have any shape that substantially corresponds to the curvature of the eye.

Figure 10:
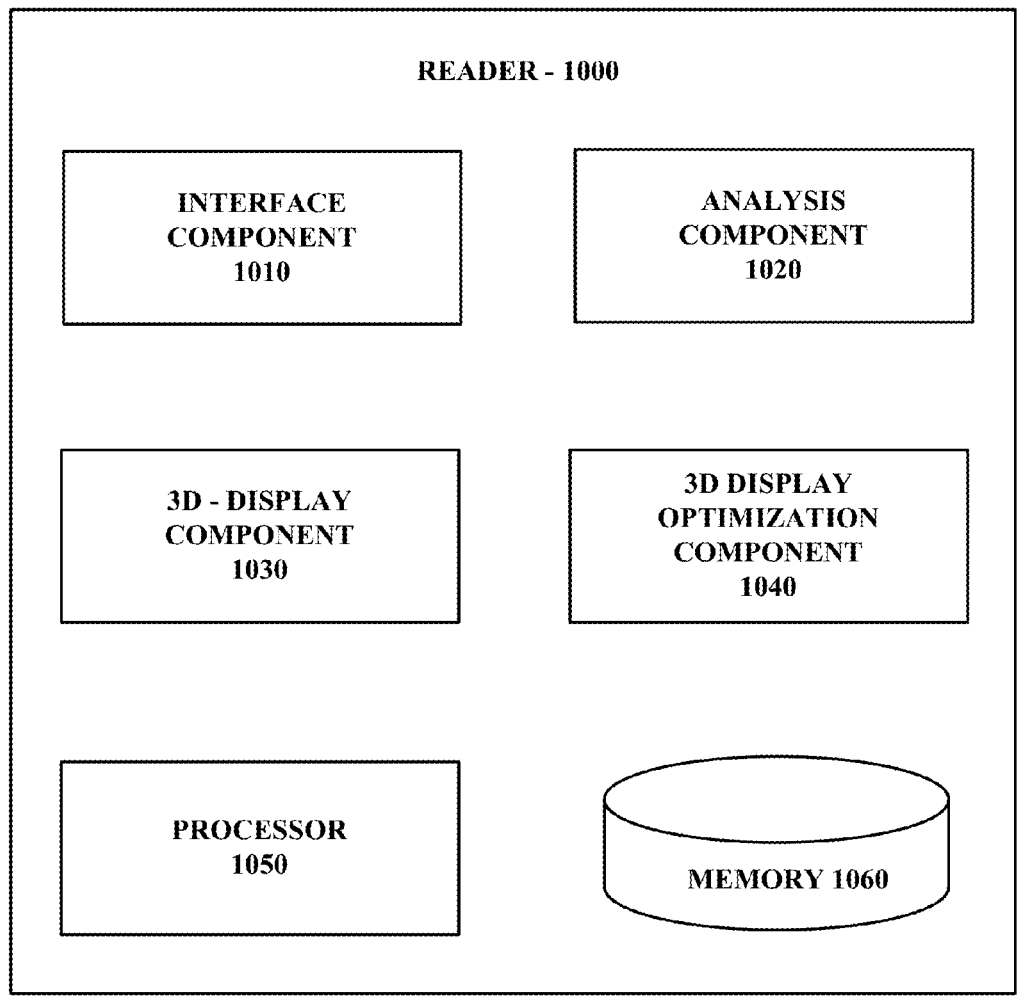
FIG. 10 presents an exemplary reader device for receiving information from a contact lens related to a wearer's current focal distance in accordance with aspects described herein.

FIG. 10 is an illustration of an exemplary non-limiting reader device 1000 that interfaces with one or two contact lenses worn by an individual and configured to generate data related to a FD of the individual. In various aspects, the reader device 1000 can include one or more of the structure and/or functionality of reader device 128 and 222 (and vice versa).

As shown in FIG. 10, reader device 1000 can include interface component 1010, analysis component 1020, three dimensional (3D) display component 1030 and 3D display optimization component 1040. Aspects of device 1000 constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described. Device 1000 can include memory 1060 for storing computer executable components and instructions. A processor 1050 can facilitate operation of the computer executable components and instructions by device 1000.

Interface component 1010 interfaces with and receives from at least one contact lens, data relating to an FD of the wearer. In particular, interface component 1010 can interface with contact lenses described herein that comprise a vergence component (e.g. vergence component 310 and the like) and a contact lens circuit (e.g. contact lens circuit 302 and the like). In an aspect, interface component 1010 employs a receiving component, such as an RF receiver, transceiver, photodetector, or IR receiver, to receive sensed and/or determined information from a contact lens comprising a contact lens circuit and vergence component as described herein. In some aspects, interfacing component 1010 can receive determined or inferred information relating to the wearer's FD. According to this aspect, the contact lens can include appropriate circuitry and components to process data sensed by one or more sensors provided on or within the contact lens.

In another aspect, the reader 1000 can receive raw data from a contact lens relating to information generated by a vergence component of the contact lens. For example, the interface component 1010 can receive signals indicating movement of the left and/or right eyes of an individual, a position of a left eye, and/or a position of the right eye. According to this embodiment, the reader 1000 comprises an analysis component 1020 that can analyze the received raw data to determine or infer the individuals FD.

Analysis component 1020 can employ same or similar functionality described with reference to processor 502. In particular, analysis component 1020 can employ received information relating to movement and positions of the eyes of an individual to determine and/or infer when the eyes are performing vergence movement's, when the eyes have reached convergence, and a FD of the individual when the eyes have reached convergence. In order to processes received information generated by vergence components of the left and/or right contact lenses of an individual, in an aspect, received information can be stored in memory 1060. Further, memory 1060 can store various look-up tables and/or algorithms (as discussed with respect to processor memory 504) relating eye movement and position information to an individual's FD.

Reader 1000 can further include a 3D display component configured to generate a 3D image. In an aspect, the 3D image is part of an augmented reality display that includes imaginary objects projected into a real world environment. For example, reader 1000 can include an augmented reality head-mounted display configured to project imaginary objects onto a real world physical environment of an individual as the individual move about the environment.

Reader 1000 can further include a 3D display optimization component 1040 configured to optimize a 3D display generated by 3D display component 1030. In particular, 3D display optimization component 1040 is configured to determine placement of imaginary objects of a 3D display based on a viewer's focal distance. For example, if a user is focusing on an object F at a distance H (where H can include an individual's FD or FP), the 3D optimization component can direct 3D display component to generate an imaginary object at distance H. According to this example, the 3D display component can generate an imaginary image of a cat climbing a real physical tree located at distance H. In another example if user is focusing on an object P at distance M, the 3D display optimization component 1040 can determine size and placement of imaginary objects within a 3D display associated with object P such that the imaginary objects are appropriately scaled and dispersed within the 3D display in accordance with the viewer's perspective as if the objects where actually present in the viewer's real physical environment.

In various aspects, the 3D display optimization component 1040 can employ various (explicitly or implicitly trained) classification schemes or systems (e.g., support vector machines, neural networks, expert systems, Bayesian belief networks, fuzzy logic, data fusion engines, etc.) in connection with determining proper placement and scaling of imaginary objects within a 3D display based on a viewer's current FD. A classifier can map an input attribute vector, x=(x1, x2, x3, x4 . . . , xn), to a confidence that the input belongs to a class, such as by f(x)=confidence(class). Such classification can employ a probabilistic or statistical-based analysis (e.g., factoring into the analysis utilities and costs) to prognose or infer a state of a retina. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used in this disclosure also is inclusive of statistical regression that is utilized to develop models of priority.

Figure 11:
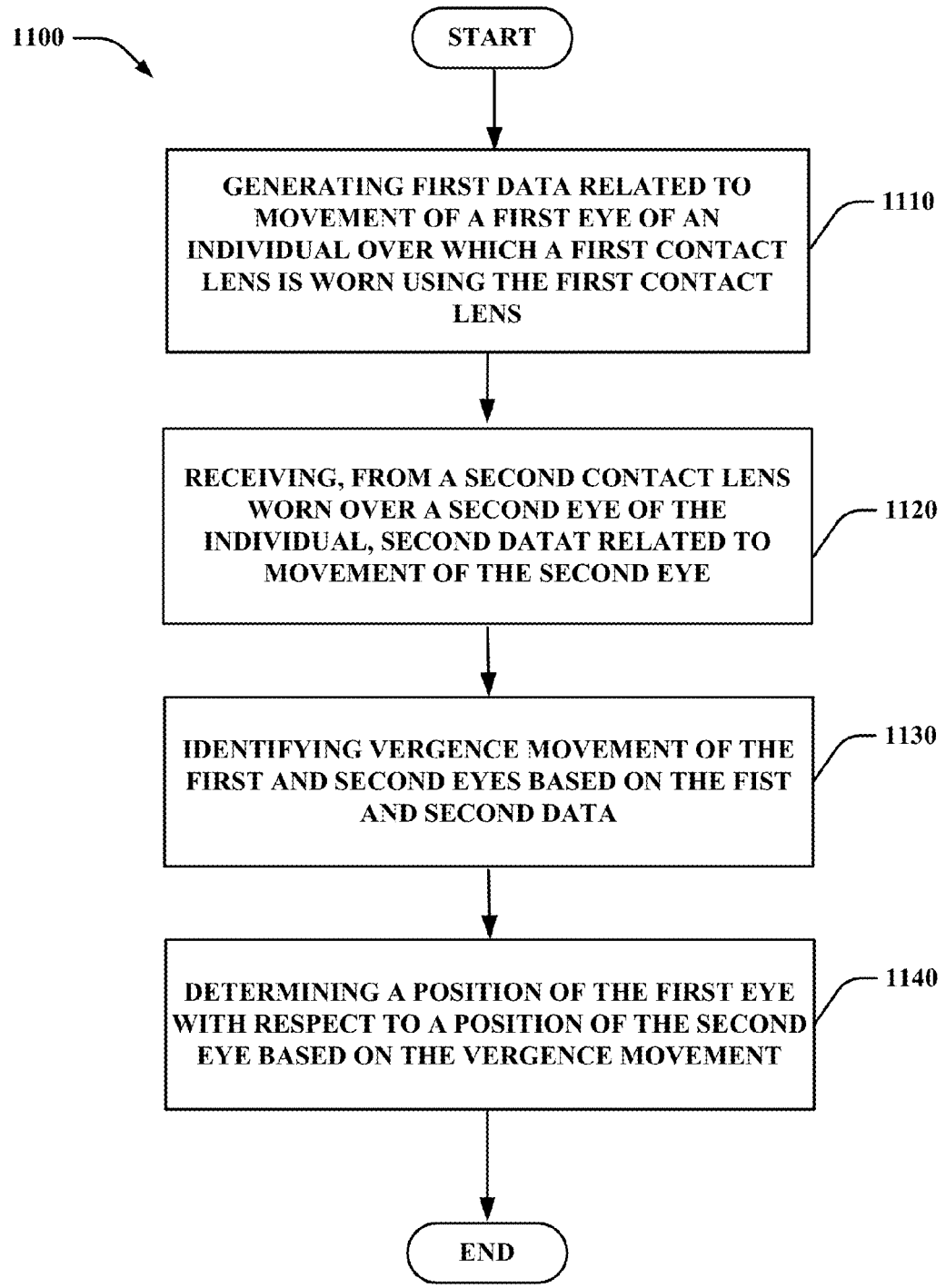
FIG. 11 is an exemplary flow diagram of a method for generating data related to an individual's current focal distance using one or two contact lenses, in accordance with aspects described herein.
Figure 12:
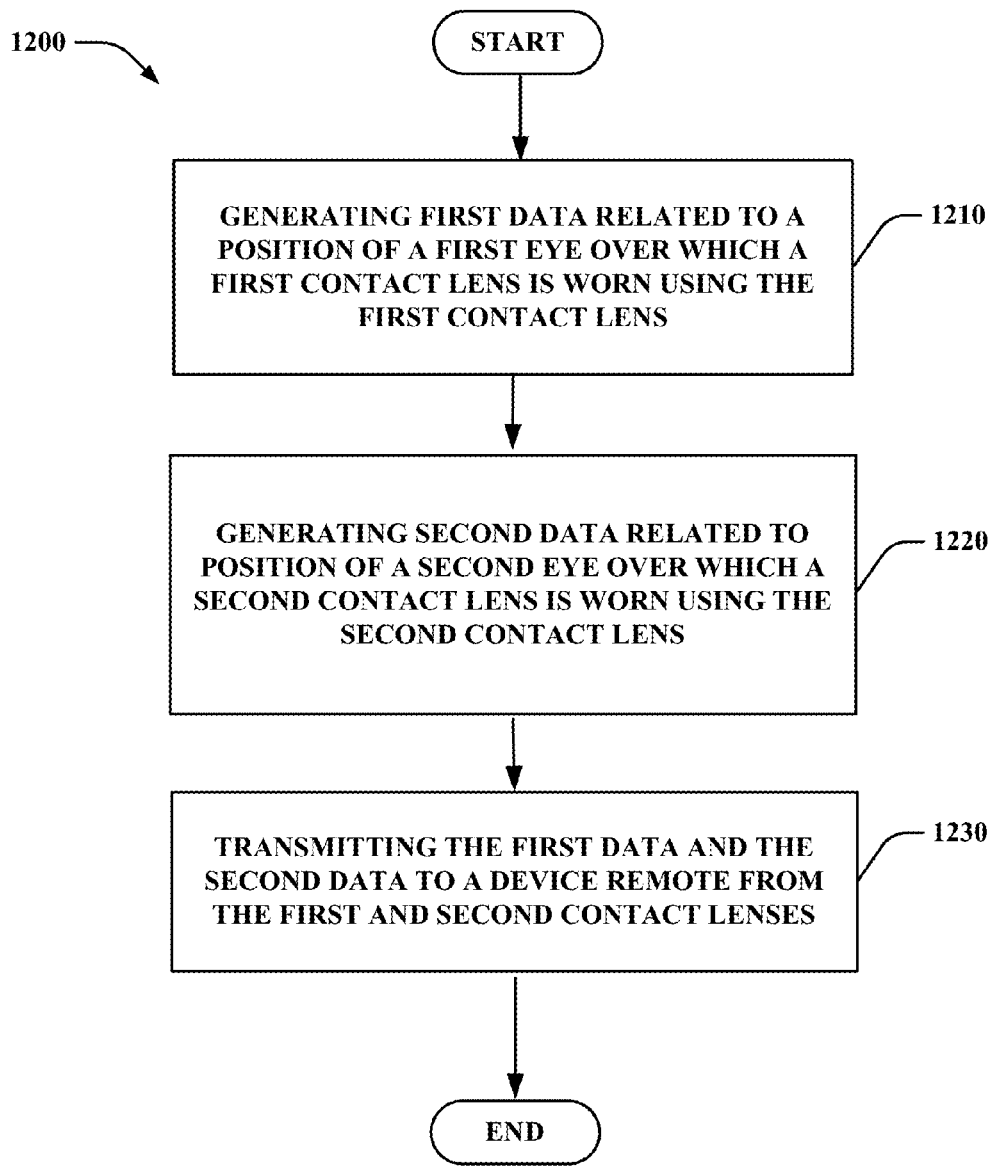
FIG. 12 is another exemplary flow diagram of a method for generating data related to an individual's current focal distance using one or two contact lenses, in accordance with aspects described herein.
Figure 13:
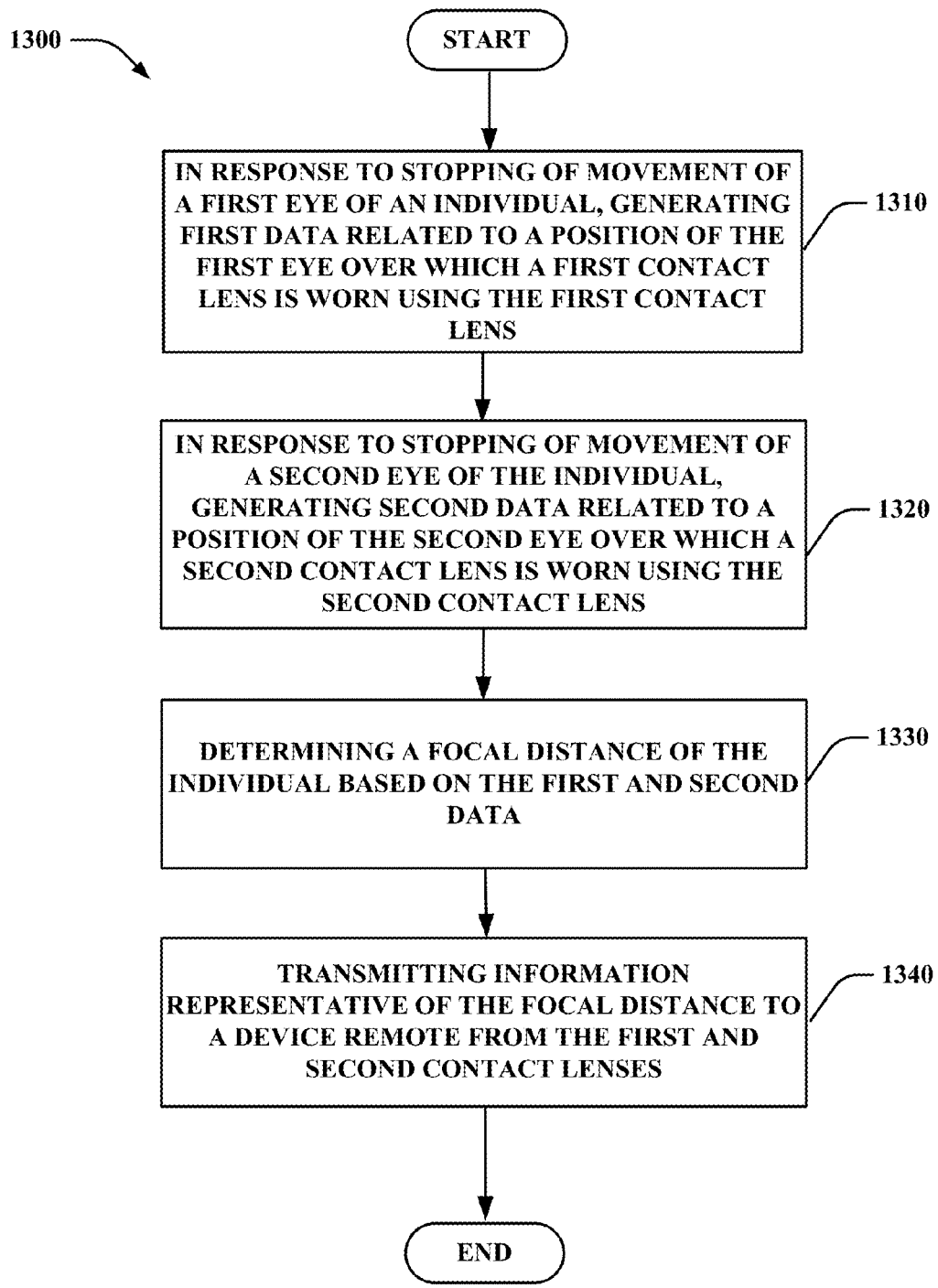
FIG. 13 is another exemplary flow diagram of a method for generating data related to an individual's current focal distance using one or two contact lenses, in accordance with aspects described herein.

FIGS. 11-13 illustrates methodologies or flow diagrams in accordance with certain aspects of this disclosure. While, for purposes of simplicity of explanation, the methodologies are shown and described as a series of acts, the disclosed subject matter is not limited by the order of acts, as some acts may occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Referring now to FIG. 1, presented is a flow diagram of an example application of contact lenses disclosed in this description in accordance with an embodiment. In an aspect, in exemplary methodology 1100, a contact lens such as those described herein (e.g. 500 and the like) facilitate determining a wearer's current focal distance. At 1110, first data is generated related to movement of a first eye of an individual over which a first contact lens is worn using the first contact lens (e.g. using vergence component 310 and the like). At 1120, second information is received from a second contact lens of the individual, the second information relating to movement of the second eye (e.g. using communication component 304 and/or receiving component 404). At 1130, vergence movement of the first and second eyes is identified based on the first and second data (e.g. using processor 502). At 1140, a position of the first eye with respect to a position of the second eye is determined based on the vergence movement (e.g. using processor 502).

Turning now to FIG. 12, presented is another flow diagram of an example application of systems and contact lenses disclosed in this description in accordance with an embodiment. In an aspect, in exemplary methodology 1200, a contact lens such as those described herein (e.g. contact lens 300 and the like) generate data related to a FD of the wearer. At 1210, first data is generated relating to a position of a first eye of an individual over which a first contact lens is worn using the first contact lens (e.g. using vergence component 310). At 1220, second data is generated relating to a position of a second eye of the individual over which a second contact lens is worn using the second contact lens (e.g. using vergence component 310). Then at 1230 the first data and the second data are transmitted to a device remote from the first and second contact lenses (e.g. using communication component 304).

Turning now to FIG. 13, presented is another flow diagram of an example application of systems and contact lenses disclosed in this description in accordance with an embodiment. At 1310, first data is generated relating to a position of a first eye of an individual over which a first contact lens is worn, in response to stopping of movement of the first eye, using the first contact lens (e.g. using vergence component 310). At 1320, second data is generated relating to a position of a second eye of an individual over which a second contact lens is worn, in response to stopping of movement of the second eye, using the second contact lens (e.g. using vergence component 310). At 1330, a focal distance of the individual is determined based on the first and second data (e.g. using processor 502). Then at 1340, information representative of the focal distance of the individual is transmitted to a device remote from the first and second contact lenses (e.g. using communication component 304).

Exemplary Networked and Distributed Environments

Figure 14:
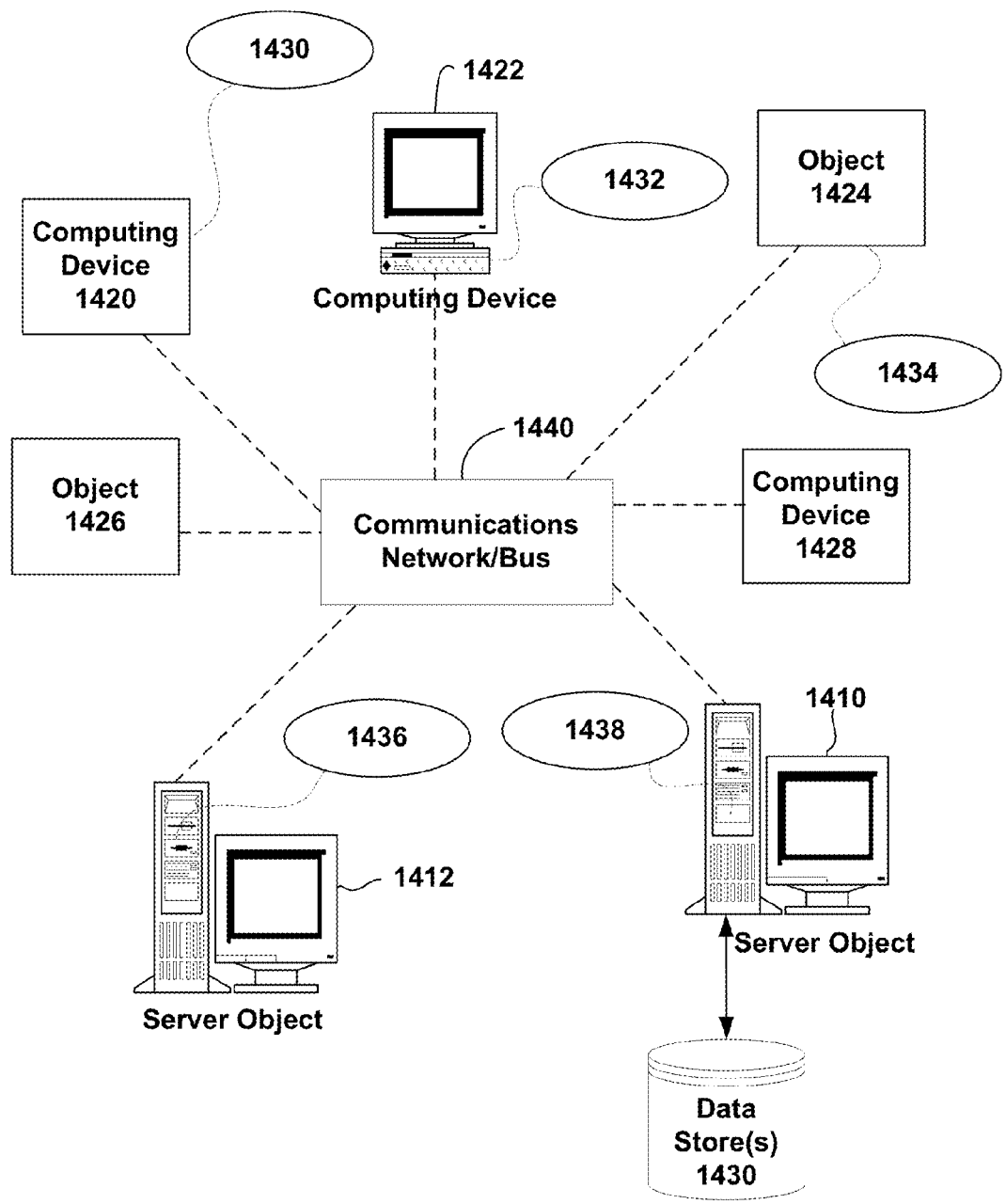
FIG. 14 is an illustration of a schematic diagram of an exemplary networked or distributed computing environment with which one or more aspects described herein can be associated.

FIG. 14 provides a schematic diagram of an exemplary networked or distributed computing environment with which one or more aspects described in this disclosure can be associated. The distributed computing environment includes computing objects 1410, 1412, etc. and computing objects or devices 1420, 1422, 1424, 1426, 1428, etc., which can include programs, methods, data stores, programmable logic, etc., as represented by applications 1430, 1432, 1434, 1436, 1438. It can be appreciated that computing objects 1410, 1412, etc. and computing objects or devices 1420, 1422, 1424, 1426, 1428, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 1410, 1412, etc. and computing objects or devices 1420, 1422, 1424, 1426, 1428, etc. can communicate with one or more other computing objects 1410, 1412, etc. and computing objects or devices 1420, 1422, 1424, 1426, 1428, etc. by way of the communications network 1440, either directly or indirectly. Even though illustrated as a single element in FIG. 14, network 1440 can include other computing objects and computing devices that provide services to the system of FIG. 14, and/or can represent multiple interconnected networks, which are not shown.

In a network environment in which the communications network/bus 1440 can be the Internet, the computing objects 1410, 1412, etc. can be Web servers, file servers, media servers, etc. with which the client computing objects or devices 1420, 1422, 1424, 1426, 1428, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens). In various aspects, the data store can include or be included within, any of the memory described herein, any of the contact lenses described herein. In various aspects, the data store can be any repository for storing information transmitted to or received from the contact lens.

Figure 15:
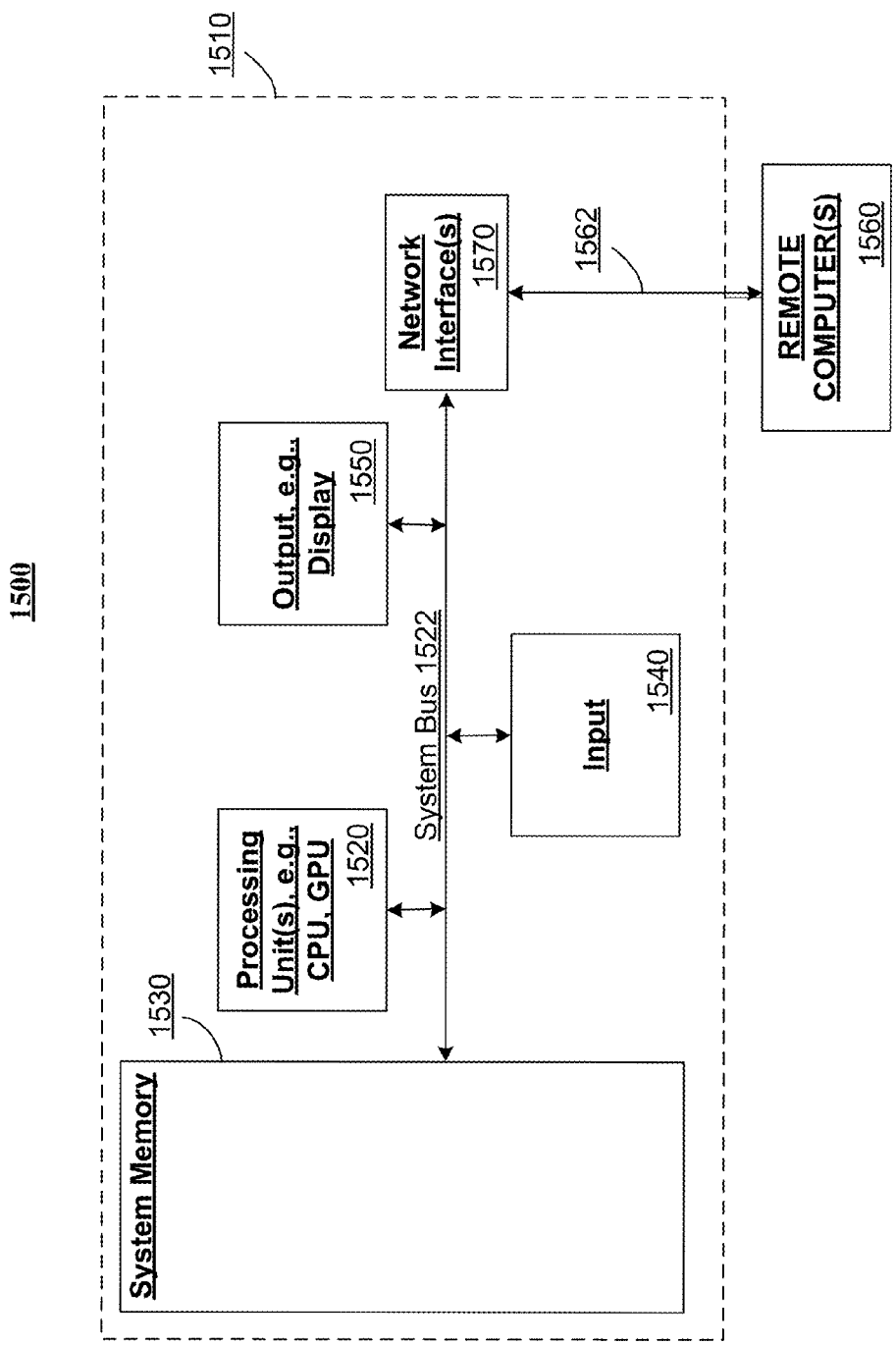
FIG. 15 is an illustration of a schematic diagram of an exemplary computing environment with which one or more aspects described herein can be associated.

FIG. 15 illustrates an example of a suitable computing system environment 1500 in which one or aspects of the aspects described in this disclosure can be implemented. Components of computer 1510 can include, but are not limited to, a processing unit 1520, a system memory 1530, and a system bus 1522 that couples various system components including the system memory to the processing unit 1520.

Computer 1510 typically includes a variety of computer readable media and can be any available media that can be accessed by computer 1510. The system memory 1530 can include computer storage media in the form of volatile and/or nonvolatile memory such as read only memory (ROM) and/or random access memory (RAM). By way of example, and not limitation, memory 1530 can also include an operating system, application programs, other program components, and program data.

A user can enter commands and information into the computer 1510 through input devices 1540 (e.g., keyboard, keypad, a pointing device, a mouse, stylus, touchpad, touch screen, motion detector, camera, microphone or any other device that allows the user to interact with the computer 1510). A monitor or other type of display device can be also connected to the system bus 1522 via an interface, such as output interface 1550. In addition to a monitor, computers can also include other peripheral output devices such as speakers and a printer, which can be connected through output interface 1550.

The computer 1510 can operate in a networked or distributed environment using logical connections to one or more other remote computers, such as remote computer 1560. The remote computer 1560 can be a personal computer, a server, a router, a network PC, a peer device or other common network node, or any other remote media consumption or transmission device, and can include any or all of the elements described above relative to the computer 1510. The logical connections depicted in FIG. 15 include a network 1570, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and non-volatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:
1. A system, comprising:
 a first contact lens and a second contact lens respectively configured to be worn over first and second eyes of an individual, wherein the first contact lens and the second contact lens respectively comprise:
first and second substrates; and
first and second circuits respectively disposed on or within the first and second substrates and configured to respectively generate first data related to a focal trajectory of the first eye and second data related to focal trajectory of the second eye, wherein the first circuit employs the second contact lens to generate the first data and the second circuit employs the first contact lens to generate the second data.

2. The system of claim 1, wherein the first and second circuits are configured to generate the first and second data respectively in response to movement of the first and second eyes.

3. The system of claim 2, wherein the movement is vergence movement of the first and second eyes.

4. The system of claim 1, wherein the first and second contact lenses respectively comprise first and second communication components configured to at least one of: transmit information to one another, or transmit information to an external device.

5. The system of claim 1, wherein the first contact lens comprises a communication component configured to wirelessly transmit the first data to the second contact lens, and wherein the second contact lens comprises a communication component configured to wirelessly transmit the first and second data to an external device.

6. The system of claim 1, wherein the first contact lens comprises a communication component configured to wirelessly transmit the first data to the second contact lens, and wherein the second contact lens comprises a processor configured to determine the individual's current focal distance based on the first and second data.

7. The system of claim 1, wherein,
the first circuit component comprises one or more sensors configured to generate first movement data related to movement of the first contact lens and a communication component configured to transmit the first movement data to the second circuit;
the second circuit comprises one or more sensors configured to generate second movement data related to movement of the second contact lens and a communication component configured to transmit the second movement data to the first circuit; and
wherein the first circuit generates the first data based on the first movement data and the second movement data, and the second circuit generates the second data based on the first movement data and the second movement data.

8. A contact lens, comprising:
a contact lens configured to be worn over a first eye of an individual, the contact lens comprising:
a substrate;
a vergence component disposed on or within the substrate and configured to generate data related to movement of the first eye;
a communication component configured to receive, from a second contact lens worn over a second eye of the individual, second data related to movement of the second eye; and
a processor configured to identify vergence movement of the first and second eyes based on the first and second data, and determine position of the first eye with respect to a position of the second eye based on the vergence movement.

9. The contact lens of claim 8, wherein the processor is configured to identify initiation of the vergence movement and stopping of the vergence movement based on the first and second data and determine the position of the first eye with respect to the position of the second eye at a time of stopping of the vergence movement.

10. The contact lens of claim 8, wherein the first vergence component comprises one or more sensors configured to generate the first data related to the movement of the first eye.

11. The contact lens of claim 10, wherein the one or more sensors include at least one of: a gyroscopic sensor, or an accelerometer.

12. The contact lens of claim 8, wherein the vergence component further comprises:
a signal emitting component configured to project a first signal away from the first eye and towards the second eye; and
a signal receiving component configured to receive a reflected signal generated in response to reflection of the first signal off of the second eye;
wherein the processor is configured to determine time of flight information based on the first signal and the reflected signal, and wherein the processor is configured to identify the vergence movement based on the time of flight information.

13. The contact lens of claim 8, wherein the processor is configured to determine the individual's current focal distance based on the position of the first eye with respect to the position of the second eye.

14. The contact lens of claim 8, wherein the communication component is configured to transmit the information representative of the position of the first eye with respect to the position of the second eye to an external device that is not disposed on or within a contact lens.

15. A method comprising:
generating first data related to position of a first eye over which a first contact lens is worn using the first contact lens;
generating second data related to position of a second eye over which a second contact lens is worn using the second contact lens; and
transmitting the first data and the second data to a device remote from the first and second contact lenses.

16. The method of claim 15, further comprising:
detecting movement of the first eye and the second eye and generating the first data and the second data in response to the detecting.

17. The method of claim 16, wherein the detecting comprises employing one or more sensors disposed on the first and second contact lenses.

18. The method of claim 16, further comprising:
transmitting the first data from the first contact lens to the second contact lens;
comparing the first data with the second data; and
determining that the first and second eyes have reached convergence based on the comparing.

19. The method of claim 18, further comprising:
in response to the determining that the first and second eyes have reached convergence, determining a focal distance of a wearer of the first and second contact lenses based on the first data and the second data.

20. The method of claim 15, wherein the generating the first data comprises:
emitting a signal from the first contact lens to the second contact lens;
receiving a reflected signal at the first contact lens in response to reflection of the signal off of the second contact lens;

determining time of flight information based on the signal and the reflected signal; and generating the first data based on the time of flight information.

* * * * *